US010723730B2

(12) United States Patent
Chekal et al.

(10) Patent No.: US 10,723,730 B2
(45) Date of Patent: Jul. 28, 2020

(54) SOLID FORMS OF A SELECTIVE CDK4/6 INHIBITOR

(71) Applicant: PFIZER INC., New York, NY (US)

(72) Inventors: Brian Patrick Chekal, Niantic, CT (US); Nathan D. Ide, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/808,577

(22) Filed: Nov. 9, 2017

(65) Prior Publication Data

US 2018/0065964 A1    Mar. 8, 2018

Related U.S. Application Data

(63) Continuation of application No. 14/769,038, filed as application No. PCT/IB2014/058865 on Feb. 8, 2014.

(60) Provisional application No. 61/767,761, filed on Feb. 21, 2013.

(51) Int. Cl.
    *C07D 471/04*    (2006.01)

(52) U.S. Cl.
    CPC .................. *C07D 471/04* (2013.01)

(58) Field of Classification Search
    CPC .................................. C07D 471/04
    See application file for complete search history.

(56) References Cited

U.S. PATENT DOCUMENTS

| | | | |
|---|---|---|---|
| 6,936,612 B2 | 8/2005 | Barvian et al. |
| 7,208,489 B2 | 4/2007 | Barvian et al. |
| 7,345,171 B2 | 3/2008 | Beylin et al. |
| 7,456,168 B2 | 11/2008 | Barvian et al. |
| 7,781,583 B2 | 8/2010 | Erdman et al. |
| 7,863,278 B2 | 1/2011 | Beylin et al. |

FOREIGN PATENT DOCUMENTS

| | | |
|---|---|---|
| WO | 2003/062236 | 7/2003 |
| WO | 2005/005426 | 1/2005 |
| WO | 2008/032157 | 3/2008 |
| WO | 2016/024249 | 2/2016 |

OTHER PUBLICATIONS

International Search Report dated Apr. 7, 2014 for PCT/IB2004/002152, filed Jun. 28, 2004 and Published on Jan. 20, 2005 as WO 2005/005426.
Written Opinion dated Apr. 7, 2014 for PCT/IB2004/002152, filed Jun. 28, 2004 and Published on Jan. 20, 2005 as WO 2005/005426.
Communication from the European Patent Office dated Aug. 23, 2016 in related European Patent Application No. 14705884.6 filed Aug. 2, 2014 and published as EP2958916 on Dec. 30, 2015.
International Search Report dated Oct. 22, 2018 for EP 18186675.7, filed Jul. 21, 2018.
Response dated Dec. 23, 2016 regarding communication from the European Patent Office dated Aug. 23, 2016 in related European Patent Application No. 14705884.6 filed Aug. 2, 2014 and published as EP2958916 on Dec. 30, 2015.
U.S. Appl. No. 15/578,410, filed Nov. 30, 2017.
U.S. Appl. No. 16/048,143, filed Jul. 27, 2018.
B.P. Chekal et. al., "Palbociclib Commerical Manufacturing Process Development. Part III. Deprotection Followed by Crystallization for API Particle Property Control" Org Proc Res Dev 2016, 20, 1217-1226.
Communication of a notice of opposition filed by Galenicum Health S.L.U., from the European Patent Office dated Jun. 18, 2019 in related European Patent Application No. 14705884.6 filed Aug. 2, 2014 and published as EP2958916 dated Dec. 30, 2015.
Communication of a notice of opposition filed by Teva Pharmaceutical Industries Ltd., from the European Patent Office dated Jun. 18, 2019 in related European Patent Application No. 14705884.6 filed Aug. 2, 2014 and published as EP2958916 dated Dec. 30, 2015.
Communication of a notice of opposition filed by Generics [UK] Limited, from the European Patent Office dated Jun. 18, 2019 in related European Patent Application No. 14705884.6 filed Aug. 2, 2014 and published as EP2958916 dated Dec. 30, 2015.
David W. Fry et al., "Specific inhibition of cyclin-dependent kinase 4/6 by PD 0332991 and associated antitumor activity in human tumor xenografts" Mol Cancer Ther 2004, 3, 1427-1437.

(Continued)

*Primary Examiner* — Sahar Javanmard
(74) *Attorney, Agent, or Firm* — Leslie A. Robinson

(57) ABSTRACT

This invention relates to the crystalline free base of acetyl-8-cyclopentyl-5-methyl-2-(5-piperazin-1-yl-pyridin-2-ylamino)-8H-pyrido[2,3-d]pyrimidin-7-one, formula (1) having improved properties, to pharmaceutical compositions and dosage forms comprising the free base, and to methods for making and using such compounds, compositions and dosage forms in the treatment of cell proliferative diseases, such as cancer.

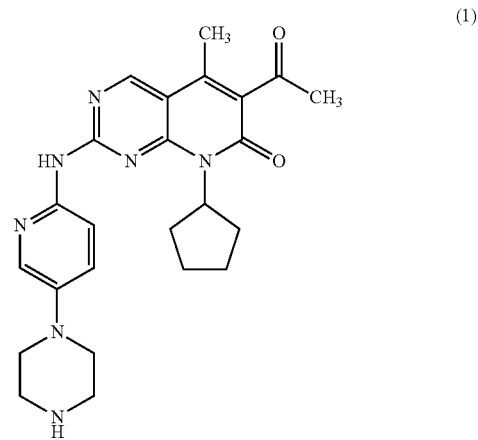

(1)

21 Claims, 9 Drawing Sheets

(56) References Cited

OTHER PUBLICATIONS www.clinicaltrial.gov; Identifier NCT01844323 "A Study in Healthy Volunteers to Estimate the Effect of the Active Ingredient Particle Size and Percentage of the Excipients Used to Formulate the Capsules in the Dissolution Rate of the Formulations in the Gastrointestinal Tract" Available from: https://clinicaltrials.gov/ct2/show/NCT01844323.

SOLID FORMS OF A SELECTIVE CDK4/6 INHIBITOR

CROSS-REFERENCE TO RELATED APPLICATIONS

This application is a continuation of U.S. patent application Ser. No. 14/769,038, filed on Aug. 19, 2015, which is the U.S. National Phase under 35 U.S.C. 371 of Patent Cooperation Treaty Patent Application No. PCT/IB2014/058865, filed Feb. 8, 2014, which claims the benefit of priority to U.S. Provisional Application No. 61/767,761, filed on Feb. 21, 2013, the contents of each of which are incorporated by reference herein in their entirety.

FIELD OF THE INVENTION

This invention relates to the free base of 6-acetyl-8-cyclopentyl-5-methyl-2-(5-piperazin-1-yl-pyridin-2-ylamino)-8H-pyrido[2,3-d]pyrimidin-7-one having improved physicochemical properties. The invention also relates to pharmaceutical compositions and dosage forms comprising the free base, and to methods for making and using such compounds, compositions and dosage forms in the treatment of cell proliferative diseases, such as cancer.

BACKGROUND OF THE INVENTION

The compound 6-acetyl-8-cyclopentyl-5-methyl-2-(5-piperazin-1-yl-pyridin-2-ylamino)-8H-pyrido[2,3-d]pyrimidin-7-one (also referred to herein as "compound 1"), may be represented by the structure:

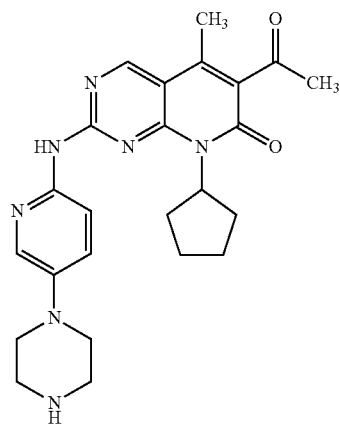

and is also known as palbociclib or PD-0332991. Compound 1 is a potent and selective inhibitor of CDK4 and CDK6.

Compound 1 and pharmaceutically acceptable salts thereof are disclosed in International Publication No. WO 2003/062236 and U.S. Pat. Nos. 6,936,612, 7,208,489 and 7,456,168, which describe the preparation of compound 1 as its hydrochloride salt. International Publication No. WO 2005/005426 and U.S. Pat. Nos. 7,345,171 and 7,863,278 describe preparation of the free base and various mono- and di-acid addition salts of compound 1, including polymorphic forms of the isethionate salt. A process for the preparation of compound 1 as a mono-isethionate salt is described in International Publication No. WO 2008/032157 and U.S. Pat. No. 7,781,583. The contents of each of the foregoing references are incorporated herein by reference in their entirety.

While compound 1 is a potent and selective CDK4/CDK6 inhibitor, its use as a free base presented challenges for pharmaceutical development. The free base provided by traditional salt break procedures, e.g., as in Example 4 of WO 2005/005426, was highly static prone and formed small primary particles, which agglomerated into large, hard agglomerates that were difficult to disperse by sieving and were unsuitable for further development. The present invention provides compound 1 free base having larger primary particle size that demonstrates improved physicochemical and manufacturability properties.

SUMMARY OF THE INVENTION

The free base of compound 1, 6-acetyl-8-cyclopentyl-5-methyl-2-(5-piperazin-1-yl-pyridin-2-ylamino)-8H-pyrido[2,3-d]pyrimidin-7-one, can exist in one or more polymorphic forms, including Form A and Form B, wherein Form A is the more stable crystalline form. The free base may be anhydrous, or may contain varying amounts of water or one or more solvents.

The present invention provides the crystalline free base of compound 1 having larger primary particle size, greatly reduced specific surface area, and lower surface energy measurements than the free base provided by traditional salt break methods described in the art. The large particle size compound 1 free base disclosed herein is distinguishable by a variety of methods.

The polymorphic and solid forms of the invention can be distinguished by powder X-ray diffractometry (PXRD), solid state NMR (ssNMR), differential scanning calorimetry (DSC), vibrational spectroscopy (e.g., IR and Raman spectroscopy), polarized light microscopy (PLM), scanning electron microscopy (SEM), hot stage optical microscopy, electron crystallography, single crystal X-ray diffractometry, quantitative analysis, particle size analysis (PSA) (e.g., particle size, particle size distribution (PSD), and particle shape), specific surface area (SSA) analysis, surface energy analysis (e.g., inverse gas chromatography or IGC), by solubility studies and dissolution studies, or a combination of these techniques.

In one aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one having a specific surface area of ≤2 m$^2$/g. In some embodiments, the free base has a specific surface area of ≤1 m$^2$/g.

In preferred embodiments, the crystalline free base of compound 1 is a polymorph Form A of the free base. In some such embodiments, the crystalline free base has a PXRD pattern comprising a peak at diffraction angle (2θ) of 10.1±0.2. In other such embodiments, the crystalline free base has a PXRD pattern comprising peaks at diffraction angles (2θ) of 8.0±0.2 and 10.1±0.2. In still other embodiments, the crystalline free base has a PXRD pattern comprising peaks at diffraction angles (2θ) of 8.0±0.2, 10.1±0.2, and 11.5±0.2. In further embodiments, the crystalline free base has a PXRD pattern comprising peaks at diffraction angles (2θ) of 8.0±0.2, 10.1±0.2, 10.3±0.2, and 11.5±0.2. In further embodiments, the crystalline free base has a PXRD pattern comprising peaks at diffraction angles (2θ) essentially the same as shown in FIG. 1.

In some embodiments, the crystalline free base of compound 1 (Form A) has a $^{13}$C solid state NMR (ssNMR) spectrum comprising the following resonance (ppm) values: 12.5 ppm±0.2 ppm. In other embodiments, the crystalline free base has a $^{13}$C solid state NMR spectrum comprising the following resonance (ppm) values: 12.5 ppm and 112.4 ppm±0.2 ppm. In further embodiments, the crystalline free base has a $^{13}$C solid state NMR spectrum comprising the following resonance (ppm) values: or 12.5 ppm, 112.4 ppm and 143.2 ppm±0.2 ppm.

In some embodiments described herein, the compound 1 free base of the invention is distinguished by particle size analysis. In some such embodiments, the crystalline free base has a primary particle size of from about 5 μm to about 150 μm, preferably from about 10 μm to about 100 μm, or more preferably from about 15 μm to about 80 μm. In other such embodiments, the crystalline free base has a primary particle size distribution characterized by: (i) a D10 value of from about 5 μm to about 10 μm; (ii) a D50 value of from about 10 μm to about 45 μm; or (iii) a D90 value of from about 30 μm to about 125 μm; or a combination of (i), (ii) and (iii). In additional embodiments, the crystalline free base has a primary particle size distribution ratio of (D90–D10)/D50 of from about 2 to about 3. In further embodiments, the crystalline free base has a volume mean diameter (D[4,3]) of from about 15 μm to about 125 μm.

In some embodiments, the crystalline free base of compound 1 is anhydrous. In other embodiments, the crystalline free base of compound 1 is a solvate, in particular a hydrate.

In another aspect, the invention provides a pharmaceutical composition comprising a crystalline free base of compound 1, having the large primary particle size according to the invention, and a pharmaceutically acceptable carrier, diluent or excipient. Frequently, the pharmaceutical composition comprises polymorph Form A of the free base.

The invention further provides a capsule comprising such a pharmaceutical composition of the invention. In some such embodiments, the capsule comprises from 0.1 to 200 mg, and preferably from 25 to 150 mg, of compound 1 free base (preferably as polymorph Form A), having the large primary particle size as described herein.

In another aspect, the invention provides a method of treating cancer in a mammal, preferably a human, comprising administering to the mammal a therapeutically effective amount of a pharmaceutical composition of the invention. The method of treatment may further comprise administration of compound 1 in combination with one or more additional therapeutic agents.

In further aspects, the invention provides methods of making the free base of compound 1 having a large primary particle size, as described herein. One method involves dissolving the small particle size free base of compound 1 in mixture of a first solvent and a second solvent and heating to achieve dissolution, cooling to appropriate temperature, providing seed crystals of compound 1 free base (Form A), followed by crystallization to provide the large particle size free base of compound 1. The small particle size free base used in this process may be isolated from a traditional salt break procedure, e.g., by acidic hydrolysis of the intermediate vinyl ether to provide an acid addition salt, followed by basification, as described in Example 5. Another method involves acidic hydrolysis of the intermediate vinyl ether in a mixture of water and a first solvent, which may require heating to obtain dissolution, addition of a second solvent and basification to provide a second mixture comprising the free base generated in situ, heating if required to obtain dissolution and to distill off water, and providing seed crystals of compound 1 free base (Form A) at an appropriate temperature, followed by crystallization to provide the free base of compound 1 having a large primary particle size. The invention further provides the free base of compound 1 prepared by these methods, having the properties described herein.

In each of the above methods, the first solvent is an alcohol and the second solvent is an aromatic solvent. Suitable alcohols include, but are not limited to, relatively high boiling alcohols such as n-butanol, t-butanol, n-propanol, pentanol, 1,4-butanediol or propylene glycol, and the like. Suitable aromatic solvents include, but are not limited to, anisole, mesitylene, m-xylene, chlorobenzene, pyridine, and the like. To improve yields, the methods may include heating or cooling to temperatures above or below room temperature. Frequently, the reaction mixtures may be heated to temperatures ranging from about 30° C. to about 150° C., and more frequently from about 50° C. to about 120° C. to achieve dissolution. During crystallization, it may be desirable to cool the reaction mixture to a temperature that is at or below room temperature, for example between about 0° C. and about 30° C., preferably to about 5° C., about 10° C., about 15° C., or about 20° C.

These and other aspects and embodiments are further described by the detailed description provided herein. Each of the embodiments described herein can be combined with any other embodiment described herein not inconsistent with the embodiment with which it is combined.

DETAILED DESCRIPTION OF THE INVENTION

Figure 1:
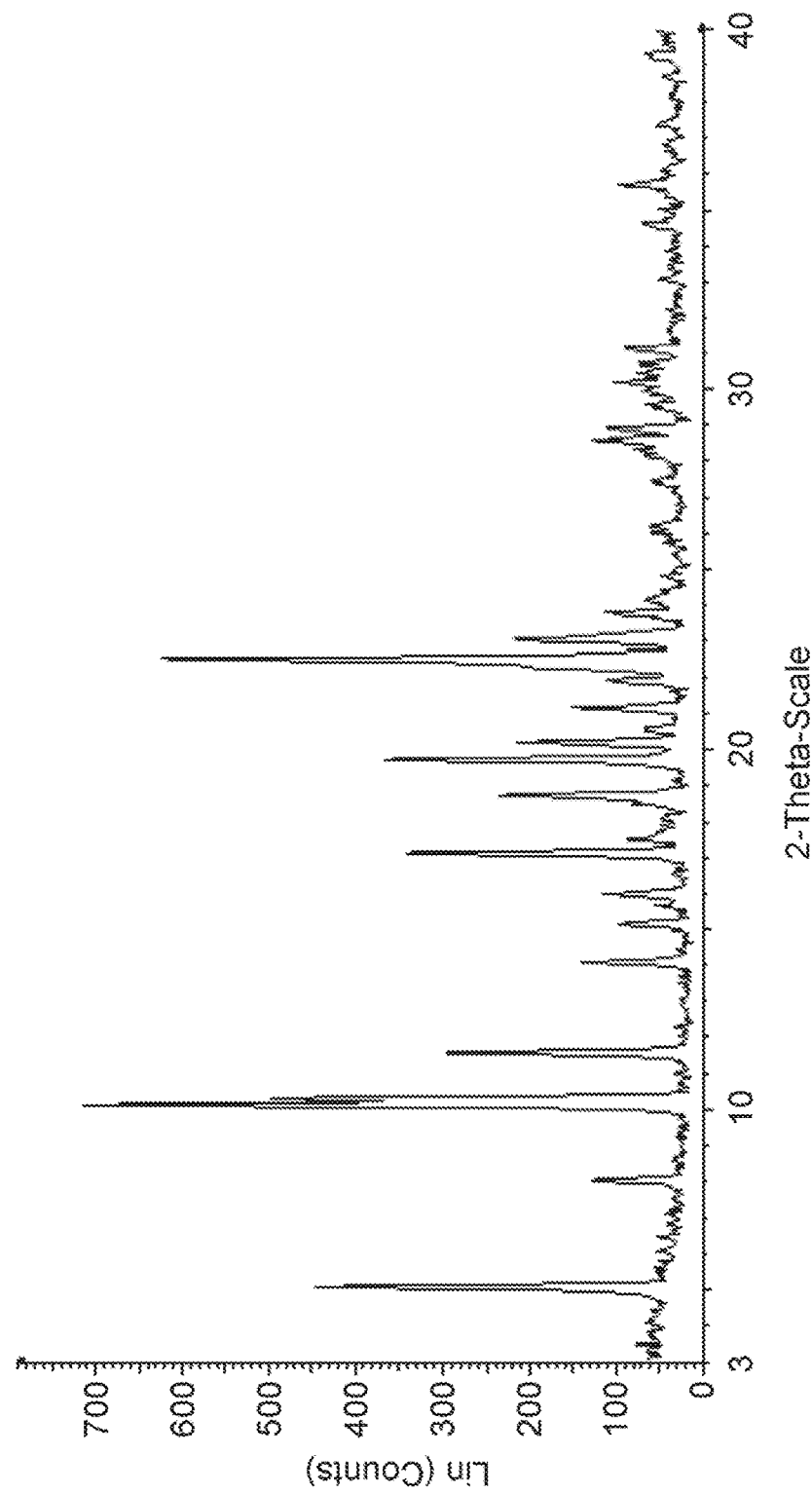
FIG. 1 shows a PXRD pattern of compound 1 free base, polymorph Form A.

The present invention may be understood more readily by reference to the following detailed description and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, the term "about" means within a statistically meaningful range of a value, such as a stated concentration range, time frame, molecular weight, particle size, temperature or pH. Such a range can be within an order of magnitude, typically within 20%, more typically within 10%, and even more typically within 5% of the indicated value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

As used herein, unless otherwise indicated, the term "abnormal cell growth" refers to cell growth that is independent of normal regulatory mechanisms (e.g., loss of contact inhibition). "Abnormal cell proliferative diseases" are diseases characterized by abnormal cell growth, such as cancer.

The term "cancer" includes both solid tumors and hematological malignancies. Cancers include, but are not limited to, breast cancer, ovarian cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma).

The phrase "pharmaceutically acceptable" refers to substances, which are within the scope of sound medical judgment, suitable for use in contact with the tissues of patients without undue toxicity, irritation, allergic response, and the like, commensurate with a reasonable benefit/risk ratio, and effective for their intended use.

The term "mammal", as used herein, may be a human or non-human mammal (e.g., dog, cat, rabbit, rat, mouse, horse, monkey, other lower-order primate, etc.). Preferably the mammal is a human.

As used herein, unless otherwise indicated, the term "treating" means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" as defined immediately above.

As used herein, an "effective" amount refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Unit dosage form", as used herein, refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject will depend upon a variety of factors including the disorder being treated and the severity of the disorder; specific composition employed; age, body weight, general health, sex and diet of the subject; time of administration, duration of the treatment; drugs and/or additional therapies used in combination or coincidental with the inventive compositions, and like factors well known in the medical arts.

As used herein, the term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.2° or 0.10. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

The term, "solvate," as used herein, refers to a crystal form of a substance which contains solvent. The term "hydrate" refers to a solvate wherein the solvent is water.

The term "seeding," as used herein, means the addition of crystals to a crystallization system, for the purpose of initiating or enhancing nucleation or acting as substrate for further crystallization.

As used herein, the terms "API" or "active pharmaceutical ingredient" refer to the free base of 6-acetyl-8-cyclopentyl-5-methyl-2-(5-piperazin-1-yl-pyridin-2-ylamino)-8H-pyrido[2,3-d]pyrimidin-7-one.

As used herein, the term "primary particles" refers to individual API crystals.

As used herein, the term "agglomerates" refers to tightly bound API crystals that are difficult to disperse into primary particles during processing and particle size analysis.

The present invention provides compound 1 free base having larger primary particle size, greatly reduced specific surface area, and lower surface energy measurements than the free base provided by traditional salt break methods. For convenience, the compound 1 free base provided by the invention may sometimes be referred to herein as the "large (primary) particle size" free base. This is in contrast to the free base of compound 1 prepared through traditional salt break methods, which is sometimes referred to as the "small (primary) particle size" free base. It will be understood by those of skill in the art that the reference to "small particle size" in this case refers to the particle size of individual API crystals, and does not take into account the propensity of the "small" particles to form large agglomerates.

In some embodiments of the invention described herein, the crystalline free base of compound 1 is distinguished by specific surface area (SSA). Thus, in one aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one having a specific surface area (SSA) of ≤2 m$^2$/g. In some embodiments, the free base has a specific surface area (SSA) of ≤1 m$^2$/g. In other embodiments, the free base of compound 1 has an SSA of ≤0.9 m²/g, ≤0.8 m²/g or ≤0.7 m²/g. In further embodiments, the free base of compound 1 has an SSA of between 0.2 m²/g and 2 m²/g, between 0.5 m²/g and 1.5 m²/g, or between 0.5 m²/g and 1 m²/g.

In some embodiments described herein, the crystalline free base of compound 1 is distinguished by dispersive surface energy. Thus, in one aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one having a dispersive surface energy of ≤60 mJ/m². In some embodiments, the free base has a dispersive surface energy of ≤55 mJ/m², ≤50 mJ/m², ≤45 mJ/m² or ≤40 mJ/m². In further embodiments, the free base of compound 1 has a dispersive surface energy of between 20 mJ/m² and 60 mJ/m², between 25 mJ/m² and 50 mJ/m², or between 30 mJ/m² and 50 mJ/m².

In preferred embodiments, the crystalline free base of compound 1 is a polymorph Form A of the free base. In some such embodiments, the crystalline form has a PXRD pattern comprising a peak at diffraction angle (2θ) of 10.1±0.2. In other such embodiments, the crystalline form has a PXRD pattern comprising peaks at diffraction angles (2θ) of 8.0±0.2 and 10.1±0.2. In still other embodiments, the crystalline form has a PXRD pattern comprising peaks at diffraction angles (2θ) of 8.0±0.2, 10.1±0.2, and 11.5±0.2. In further embodiments, the crystalline form has a PXRD pattern comprising peaks at diffraction angles (2θ) of 8.0±0.2, 10.1±0.2, 10.3±0.2, and 11.5±0.2. In other embodiments, the crystalline form has a PXRD pattern comprising peaks at diffraction angles (2θ) of 5.1±0.2, 8.0±0.2, 10.1±0.2, and 11.5±0.2. In further embodiments, the crystalline form has a PXRD pattern comprising peaks at diffraction angles (2θ) of 8.0±0.2, 10.1±0.2, 11.5±0.2, and 19.7±0.2. In still further embodiments, the crystalline form has a PXRD pattern comprising peaks at diffraction angles (2θ) of 8.0±0.2, 10.1±0.2, 11.5±0.2, and 22.5±0.2. In further embodiments, the crystalline form has a PXRD pattern comprising peaks at diffraction angles (2θ) essentially the same as shown in FIG. 1.

In some embodiments, the crystalline free base of compound 1 (Form A) has a $^{13}$C solid state NMR spectrum comprising the following resonance (ppm) values: 12.5 ppm±0.2 ppm. In other embodiments, the crystalline form has a $^{13}$C solid state NMR spectrum comprising the following resonance (ppm) values: 12.5 ppm and 112.4 ppm±0.2 ppm. In further embodiments, the crystalline form has a $^{13}$C solid state NMR spectrum comprising the following resonance (ppm) values: or 12.5 ppm, 112.4 ppm and 143.2 ppm±0.2 ppm.

In some embodiments described herein, the crystalline free base of compound 1 is distinguished by particle size analysis. In some such embodiments, the free base has a primary particle size of from about 5 μm to about 150 μm, preferably from about 10 μm to about 100 μm, and more preferably from about 15 μm to about 80 μm.

In other such embodiments, the free base has a primary particle size distribution characterized by: (i) a D10 value of from about 5 μm to about 10 μm; (ii) a D50 value of from about 10 μm to about 45 μm; or (iii) a D90 value of from about 30 μm to about 125 μm; or a combination of (i), (ii) and (iii). In additional embodiments, the free base has a primary particle size distribution ratio of (D90–D10)/D50 of from about 2 to about 3. In further embodiments, the free base has a volume mean diameter (D[4,3]) of from about 15 μm to about 125 μm.

In one aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a primary particle size of greater than about 5 μm. In some embodiments, the free base has a primary particle size of greater than about 7.5 μm. In other embodiments, the free base has a primary particle size of greater than about 10 μm. In other such embodiments, the free base has a primary particle size of greater than about 12.5 μm. In other such embodiments, the free base has a primary particle size of greater than about 15 μm.

In another aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a primary particle size of from about 5 μm to about 200 μm. In some embodiments, the free base has a primary particle size of: from about 5 μm to about 175 μm; from about 5 μm to about 150 μm; from about 5 μm to about 125 μm; from about 5 μm to about 100 μm; from about 5 μm to about 75 μm; from about 10 μm to about 200 μm; from about 10 μm to about 175 μm; from about 10 μm to about 150 μm; from about 10 μm to about 125 μm; from about 10 μm to about 100 μm; from about 10 μm to about 75 μm; from about 15 μm to about 200 μm; from about 15 μm to about 175 μm; from about 15 μm to about 150 μm; from about 15 μm to about 125 μm; from about 15 μm to about 100 μm; or from about 15 μm to about 75 μm.

In another aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a primary particle size distribution having at least one of:
  (a) a D10 value of from about 5 μm to about 10 μm;
  (b) a D50 value of from about 10 μm to about 45 μm; and
  (c) a D90 value of from about 30 μm to about 125 μm.

In some such embodiments, the free base has a D10 value of from about 5 μm to about 10 μm. In other such embodiments, the free base has a D90 value of from about 30 μm to about 125 μm. In other such embodiments, the free base has a D50 value of from about 10 μm to about 45 μm. In some such embodiments, the free base has a D10 value of from about 5 μm to about 10 μm and a D90 value of from about 30 μm to about 125 μm. In further embodiments, the free base has a D10 value of from about 5 μm to about 10 μm, a D90 value of from about 30 μm to about 125 μm, and a D50 value of from about 10 μm to about 45 μm.

In another aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a primary particle size distribution having at least one of:
  (d) a D10 value of from about 5 μm to about 10 μm;
  (e) a D50 value of from about 10 μm to about 25 μm; and
  (f) a D90 value of from about 30 μm to about 75 μm.

In some such embodiments, the free base has a D10 value of from about 5 μm to about 10 μm. In other such embodiments, the free base has a D90 value of from about 30 μm to about 75 μm. In other such embodiments, the free base has a D50 value of from about 10 μm to about 25 μm. In some such embodiments, the free base has a D10 value of from about 5 μm to about 10 μm and a D90 value of from about 30 μm to about 75 μm. In further embodiments, the free base has a D10 value of from about 5 μm to about 10 μm, a D90 value of from about 30 μm to about 755 μm, and a D50 value of from about 10 μm to about 25 μm.

In other embodiments, the free base has a primary particle size distribution having a D10 value of: from about 5 μm to about 7.5 μm; from about 5 μm to about 10 μm; from about 5 μm to about 12.5 μm; or from about 5 μm to about 15 μm.

In other embodiments, the free base has a primary particle size distribution having a D50 value of: from about 10 μm to about 50 μm; from about 10 μm to about 45 μm; from about 10 μm to about 40 μm; from about 10 μm to about 35 μm; from about 10 μm to about 30 μm; from about 10 μm to about 25 μm; or from about 10 μm to about 20 μm.

In still other embodiments, the free base has a primary particle size distribution having a D90 value of: from about 30 μm to about 175 μm; from about 30 μm to about 160 μm; from about 30 μm to about 150 μm; from about 30 μm to about 140 μm; from about 30 μm to about 130 μm; from about 30 μm to about 125 μm; from about 30 μm to about 120 μm; from about 30 μm to about 115 μm; from about 30 μm to about 110 μm; from about 30 μm to about 100 μm; from about 30 μm to about 75 μm; from about 30 μm to about 70 μm; from about 30 μm to about 65 μm; from about 30 μm to about 60 μm; from about 30 μm to about 55 μm; from about 30 μm to about 50 μm; or from about 30 μm to about 45 μm.

Each of the foregoing values of embodiments for D10 can be combined with any value for D50 and/or D90 value not inconsistent with it. Each of the foregoing values of embodiments for D50 can be combined with any value for D10 and/or D90 value not inconsistent with it. Each of the foregoing values of embodiments for D90 can be combined with any value for D10 and/or D50 value not inconsistent with it.

In another aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a primary particle size distribution ratio of (D90–D10)/D50 of from about 2 to about 3. In some such embodiments, the free base has a primary particle size of from about 5 μm to about 150 μm.

In some embodiments of this aspect, the free base has a primary particle size distribution ratio of (D90–D10)/D50 of: from about 2 to about 2.75; from about 2 to about 2.5; from about 2 to about 2.25. In other embodiments, the ratio is about 2.0, about 2.1, about 2.2, about 2.3, about 2.4, about 2.5, about 2.6, about 2.7, about 2.8, about 2.9, or about 3.0.

In yet another aspect, the invention provides a crystalline free base of 6-acetyl-8-cyclopentyl-5-methyl-2-(5-piperazin-1-yl-pyridin-2-ylamino)-8H-pyrido[2,3-d]pyrimidin-7-one, having a volume mean diameter (D[4,3]) of from about 15 μm to about 125 μm. In some embodiments, the free base has a D[4,3] of from about 50 μm to about 100 μm. In other embodiments, the free base has a D[4,3] of from about 15 μm to about 30 μm.

In still other embodiments, the free base has a D[4,3] of: from about 15 μm to about 100 μm; from about 15 μm to about 90 μm; from about 15 μm to about 80 μm; from about 15 μm to about 70 μm; from about 15 μm to about 60 μm; from about 15 μm to about 50 μm; from about 15 μm to about 40 μm; from about 25 μm to about 120 μm; from about 25 μm to about 100 μm; from about 25 μm to about 90 μm; from about 25 μm to about 80 μm; from about 25 μm to about 70 μm; from about 25 μm to about 60 μm; from about 25 μm to about 50 μm; from about 25 μm to about 40 μm; about 25 μm; about 30 μm; about 35 μm; about 40 μm; about 45 μm; about 50 μm; about 55 μm; about 60 μm; about 65 μm; about 70 μm; about 75 μm; to about 80 μm; about 90 μm; about 100 μm; about 105 μm; about 110 μm; about 115 μm; or about 120 μm.

In another aspect, the invention provides a pharmaceutical composition comprising the free base of the invention, and a pharmaceutically acceptable carrier, diluent or excipient.

The invention further provides capsule comprising such a pharmaceutical composition of the invention.

In some embodiments, the capsule comprises from 0.1 to 200 mg of polymorph Form A of 6-acetyl-8-cyclopentyl-5-methyl-2-(5-piperazin-1-yl-pyridin-2-ylamino)-8H-pyrido[2,3-d]pyrimidin-7-one. In other embodiments, the capsule comprises from 25 to 150 mg of the polymorph Form A of 6-acetyl-8-cyclopentyl-5-methyl-2-(5-piperazin-1-yl-pyridin-2-ylamino)-8H-pyrido[2,3-d]pyrimidin-7-one. In other embodiments, the capsule comprises from 50 to 150 mg of the polymorph Form A of 6-acetyl-8-cyclopentyl-5-methyl-2-(5-piperazin-1-yl-pyridin-2-ylamino)-8H-pyrido[2,3-d]pyrimidin-7-one. In other embodiments, the capsule comprises from 50 to 100 mg of the polymorph Form A of 6-acetyl-8-cyclopentyl-5-methyl-2-(5-piperazin-1-yl-pyridin-2-ylamino)-8H-pyrido[2,3-d]pyrimidin-7-one. In other embodiments, the capsule comprises from 75 to 150 mg of the polymorph Form A of 6-acetyl-8-cyclopentyl-5-methyl-2-(5-piperazin-1-yl-pyridin-2-ylamino)-8H-pyrido[2,3-d]pyrimidin-7-one In another aspect, the invention provides a method of treating cancer in a mammal, including a human, comprising administering to the mammal a therapeutically effective amount of a pharmaceutical composition of the invention. In some such embodiments, the pharmaceutical composition is administered in a capsule. The capsule may comprise from 0.1 to 200 mg of the polymorph Form A of 6-acetyl-8-cyclopentyl-5-methyl-2-(5-piperazin-1-yl-pyridin-2-ylamino)-8H-pyrido[2,3-d]pyrimidin-7-one free base. In other embodiments, the capsule may comprise from 25 to 150 mg of the polymorph Form A of 6-acetyl-8-cyclopentyl-5-methyl-2-(5-piperazin-1-yl-pyridin-2-ylamino)-8H-pyrido[2,3-d]pyrimidin-7-one free base. In further embodiments, the capsule may comprise from 50 to 150 mg of the polymorph Form A of 6-acetyl-8-cyclopentyl-5-methyl-2-(5-piperazin-1-yl-pyridin-2-ylamino)-8H-pyrido[2,3-d]pyrimidin-7-one free base.

Techniques for characterizing the crystalline free base of compound 1 according to the invention include, but are not limited to, powder X-ray diffractometry (PXRD), solid state NMR (ssNMR), differential scanning calorimetry (DSC), vibrational spectroscopy (e.g., IR and Raman spectroscopy), polarized light microscopy (PLM), scanning electron microscopy (SEM), hot stage optical microscopy, electron crystallography, single crystal X-ray diffractometry, quantitative analysis, particle size analysis (PSA) (e.g., particle size, particle size distribution (PSD), and particle shape), specific surface area (SSA) analysis, surface energy analysis (e.g., inverse gas chromatography or IGC), by solubility studies and dissolution studies, or a combination of these techniques.

In further aspects, the invention provides methods of making the free base of compound 1 having a large primary particle size, as described herein. One method involves dissolving the small particle size free base of compound 1 in mixture of a first solvent and a second solvent and heating to achieve dissolution, cooling to appropriate temperature, providing seed crystals of compound 1 free base (Form A), followed by crystallization to provide the large particle size free base of compound 1. The small particle size free base used in this process may be isolated from a traditional salt break procedure, e.g., by acidic hydrolysis of the intermediate vinyl ether to provide an acid addition salt, followed by basification, as described in Example 5.

In one embodiment, the invention provides a method of making the large particle size free base of 6-acetyl-8-cyclopentyl-5-methyl-2-(5-piperazin-1-yl-pyridin-2- ylamino)-8H-pyrido[2,3-d]pyrimidin-7-one (Form A), comprising: (a) suspending 6-acetyl-8-cyclopentyl-5-methyl-2-(5-piperazin-1-yl-pyridin-2-ylamino)-8H-pyrido[2,3-d]pyrimidin-7-one free base in mixture of a first solvent and a second solvent and heating to achieve dissolution; (b) cooling to an appropriate temperature and providing seed crystals of 6-acetyl-8-cyclopentyl-5-methyl-2-(5-piperazin-1-yl-pyridin-2-ylamino)-8H-pyrido[2,3-d]pyrimidin-7-one free base (Form A); (c) gradually cooling the mixture to achieve crystallization; and (d) isolating the free base of 6-acetyl-8-cyclopentyl-5-methyl-2-(5-piperazin-1-yl-pyridin-2-ylamino)-8H-pyrido[2,3-d]pyrimidin-7-one (Form A) having large particle size.

In another embodiment, the invention provides a method of making the large particle size free base of 6-acetyl-8-cyclopentyl-5-methyl-2-(5-piperazin-1-yl-pyridin-2-ylamino)-8H-pyrido[2,3-d]pyrimidin-7-one (Form A), comprising: (a) suspending 6-acetyl-8-cyclopentyl-5-methyl-2-(5-piperazin-1-yl-pyridin-2-ylamino)-8H-pyrido[2,3-d]pyrimidin-7-one free base in mixture of n-butanol and anisole and heating to about 95-100° C. to achieve dissolution; (b) cooling to about 80° C. and providing seed crystals of 6-acetyl-8-cyclopentyl-5-methyl-2-(5-piperazin-1-yl-pyridin-2-ylamino)-8H-pyrido[2,3-d]pyrimidin-7-one free base (Form A); (c) maintaining the mixture at about 80° C. for about 3 hours and then gradually cooling to about 10° C. to achieve crystallization; and (d) filtering to isolate the free base of 6-acetyl-8-cyclopentyl-5-methyl-2-(5-piperazin-1-yl-pyridin-2-ylamino)-8H-pyrido[2,3-d]pyrimidin-7-one (Form A) having large particle size.

Another method involves acidic hydrolysis of the intermediate vinyl ether in a mixture of water and a first solvent, which may require heating to obtain dissolution, addition of a second solvent and basification to provide a second mixture comprising the free base generated in situ, heating if required to obtain dissolution and to distill off water, cooling to appropriate temperature, providing seed crystals of compound 1 free base (Form A), followed by crystallization to provide the free base of compound 1 having a large primary particle size In one embodiment, the invention provides a method of making the large particle size free base of 6-acetyl-8-cyclopentyl-5-methyl-2-(5-piperazin-1-yl-pyridin-2-ylamino)-8H-pyrido[2,3-d]pyrimidin-7-one (Form A), comprising: (a) suspending 4-{6-[6-(1-butoxyl-vinyl)-8-cyclopentyl-5-methyl-7-oxo-7,8-dihydropyrido[2,3-d]pyrimidin-2-ylamino]-pyridin-3-yl}-piperazine-1-carboxylic acid tert-butyl ester in a mixture of water and a first solvent and heating to achieve dissolution; (b) addition of acid and reaction to produce the acid addition salt of 6-acetyl-8-cyclopentyl-5-methyl-2-(5-piperazin-1-yl-pyridin-2-ylamino)-8H-pyrido[2,3-d]-pyrimidin-7-one in situ; (c) addition of a second solvent and aqueous base to a pH of ≥10; (d) separation of the organic layer and heating to distill off water; (e) cooling to an appropriate temperature and providing seed crystals of 6-acetyl-8-cyclopentyl-5-methyl-2-(5-piperazin-1-yl-pyridin-2-ylamino)-8H-pyrido[2,3-d]pyrimidin-7-one free base (Form A); (f) gradually cooling the mixture to achieve crystallization; and (g) isolating the free base of 6-acetyl-8-cyclopentyl-5-methyl-2-(5-piperazin-1-yl-pyridin-2-ylamino)-8H-pyrido[2,3-d]pyrimidin-7-one (Form A) having large particle size.

In another embodiment, the invention provides a method of making the large particle size free base of 6-acetyl-8-cyclopentyl-5-methyl-2-(5-piperazin-1-yl-pyridin-2-ylamino)-8H-pyrido[2,3-d]pyrimidin-7-one (Form A), comprising: (a) suspending 4-{6-[6-(1-butoxyl-vinyl)-8-cyclopentyl-5-methyl-7-oxo-7,8-dihydropyrido[2,3-d]pyrimidin-2-ylamino]-pyridin-3-yl}-piperazine-1-carboxylic acid tert-butyl ester in a mixture of water and n-butanol and heating to about 70° C. to achieve dissolution; (b) addition of concentrated HCl and heating at about 70° C. for 4-6 hrs; (c) addition of anisole and aqueous NaOH to achieve a biphasic mixture having a pH of >10; (d) separation of the layers and heating the organic layer to about 120° C. to distill off water; (e) cooling to about 80° C. and providing seed crystals of 6-acetyl-8-cyclopentyl-5-methyl-2-(5-piperazin-1-yl-pyridin-2-ylamino)-8H-pyrido[2,3-d]pyrimidin-7-one free base (Form A); (g) maintaining the mixture at about 80° C. for about 3 hours and then gradually cooling to about 10° C. to achieve crystallization; and (g) filtering to isolate the free base of 6-acetyl-8-cyclopentyl-5-methyl-2-(5-piperazin-1-yl-pyridin-2-ylamino)-8H-pyrido[2,3-d]pyrimidin-7-one (Form A) having large particle size.

In some embodiments of each of the foregoing methods, the method provides the free base of compound 1 having a specific surface area of ≤2 $m^2$/g. In other embodiments of each of the foregoing methods, the method provides the free base of compound 1 having a specific surface area of ≤1 $m^2$/g. In other embodiments of each of the foregoing methods, the method provides the free base of compound 1 having a primary particle size of from about 5 μm to about 150 μm, preferably from about 10 μm to about 100 μm, and more preferably from about 15 μm to about 80 μm. In other embodiments of each of the foregoing methods, the method provides the free base of compound 1 having a primary particle size distribution characterized by: (i) a D10 value of from about 5 μm to about 10 μm; (ii) a D90 value of from about 30 μm to about 125 μm; or (iii) a D50 value of from about 10 μm to about 45 μm; or a combination of (i), (ii) and (iii).

In further embodiments of each of the foregoing methods, the method provides the free base of compound 1 having a primary particle size distribution ratio of (D90−D10)/D50 of from about 2 to about 3. In further embodiments of each of the foregoing methods, the method provides the free base of compound 1 having a volume mean diameter (D[4,3]) of from about 15 μm to about 125 μm.

In another aspect, the invention provides the free base of compound 1, as described herein, prepared according to one of these methods. In some embodiments, the invention provides the crystalline free base of 6-acetyl-8-cyclopentyl-5-methyl-2-(5-piperazin-1-yl-pyridin-2-ylamino)-8H-pyrido[2,3-d]pyrimidin-7-one (Form A), prepared according to any of the methods described herein. In some such embodiments, the free base prepared by the methods described herein may be characterized by its SSA, PSA, or surface energy, or a combination of these methods, alone or in further combination with PXRD or ssNMR. In some such embodiments, the crystalline free base has a residual solvent content of between 0.05-0.25 wt % anisole and/or between 0.05-0.25 wt % n-butanol. In other such embodiments, the crystalline free base has a residual solvent content of ≤0.5 wt % anisole and ≤0.5 wt % n-butanol, and preferably ≤0.25 wt % anisole and ≤0.25 wt % n-butanol.

In each of the above methods, the first solvent is an alcohol and the second solvent is an aromatic solvent. Suitable alcohols include, but are not limited to, relatively high boiling alcohols such as n-butanol, t-butanol, n-propanol, pentanol, 1,4-butanediol or propylene glycol, and the like. Suitable aromatic solvents include, but are not limited to, anisole, mesitylene, m-xylene, chlorobenzene, pyridine, and the like.

In some such embodiments, the solvent mixture comprises 10% alcohol, 15% alcohol, 20% alcohol, 25% alcohol, 30% alcohol, 35% alcohol, 40% alcohol, 45% alcohol, 50% alcohol, 60% alcohol, 70% alcohol, or >70% alcohol, with the balance being the aromatic solvent. In other such embodiments, the solvent mixture comprises 90% aromatic, 85% aromatic, 80% aromatic, 75% aromatic, 70% aromatic, 65% aromatic, 60% aromatic, 55% aromatic, 50% aromatic, 40% aromatic, 30% aromatic, or <30% aromatic, with the balance being the alcohol solvent.

In one preferred embodiment, the first solvent is n-butanol. In another preferred embodiment, the second solvent is anisole. In a particularly preferred embodiment, the first solvent is n-butanol and the second solvent is anisole. In some such embodiments, the solvent mixture comprises 10% n-butanol/anisole, 15% n-butanol/anisole, 20% n-butanol/anisole, 25% n-butanol/anisole, 30% n-butanol/anisole, 35% n-butanol/anisole, 40% n-butanol/anisole, 45% n-butanol/anisole, 50% n-butanol/anisole, 60% n-butanol/anisole, 70% n-butanol/anisole, or >70% n-butanol/anisole. In some preferred embodiments, the solvent mixture comprises from about 20 to about 50% n-butanol/anisole. In a particularly preferred embodiment, the solvent mixture comprises about 40% n-butanol/anisole.

To improve yields, the methods may include heating or cooling to temperatures above or below room temperature. Frequently, the reaction mixtures may be heated to temperatures ranging from about 30° C. to about 150° C., and more frequently from about 50° C. to about 120° C. to achieve dissolution. During crystallization, it may be desirable to cool the reaction mixture to a temperature that is at or below room temperature, for example between about 0° C. and about 30° C., preferably to about 5° C., about 10° C., about 15° C., or about 20° C.

In additional embodiments, the free base of compound 1 is polymorph Form A having a powder X-ray diffraction pattern comprising a peak at diffraction angle (2θ) of 10.1±0.2. In other embodiments, the crystalline form has a powder X-ray diffraction pattern comprising peaks at diffraction angles (2θ) of 10.1±0.2 and 22.5±0.2. In further embodiments of this aspect, the crystalline form has a powder X-ray diffraction pattern comprising peaks at diffraction angles (2θ) of 5.1±0.2, 10.1±0.2, and 22.5±0.2. In further embodiments, the crystalline form has a powder X-ray diffraction pattern comprising peaks at diffraction angles (2θ) of 5.1±0.2, 10.1±0.2, 19.7±0.2, and 22.5±0.2. In still other embodiments, the crystalline form has a powder X-ray diffraction pattern comprising peaks at diffraction angles (2θ) of 5.1±0.2, 10.1±0.2, 17.1±0.2, 19.7±0.2, and 22.5±0.2. In additional embodiments, the crystalline form has a powder X-ray diffraction pattern comprising peaks at diffraction angles (2θ) of 5.1±0.2, 10.1±0.2, 11.5±0.2, 17.1±0.2, 19.7±0.2, and 22.5±0.2. In yet other embodiments, the crystalline form has a powder X-ray diffraction pattern comprising peaks at diffraction angles (2θ) of 5.1±0.2, 10.1±0.2, 11.5±0.2, 17.1±0.2, 18.7±0.2, 19.7±0.2, and 22.5±0.2. In some embodiments of this aspect, the crystalline form has a powder X-ray diffraction (PXRD) pattern comprising peaks at diffraction angles (2θ) essentially the same as shown in FIG. 1.

The powder X-ray diffraction (PXRD) pattern of free base polymorph Form A is shown in FIG. 1 and the corresponding data is tabulated in Table 1.

TABLE 1

PXRD data for polymorph Form A of compound 1.

| 2θ (°) ± 0.2 | Peak Intensity (%) |
|---|---|
| 5.1 | 63 |
| 8.0 | 18 |
| 10.1 | 100 |
| 10.3 | 70 |
| 11.5 | 42 |
| 14.0 | 20 |
| 15.1 | 14 |
| 16.0 | 16 |
| 17.1 | 47 |
| 18.7 | 33 |
| 19.7 | 51 |
| 20.2 | 30 |
| 21.2 | 22 |
| 22.5 | 87 |
| 23.0 | 31 |

Figure 2:
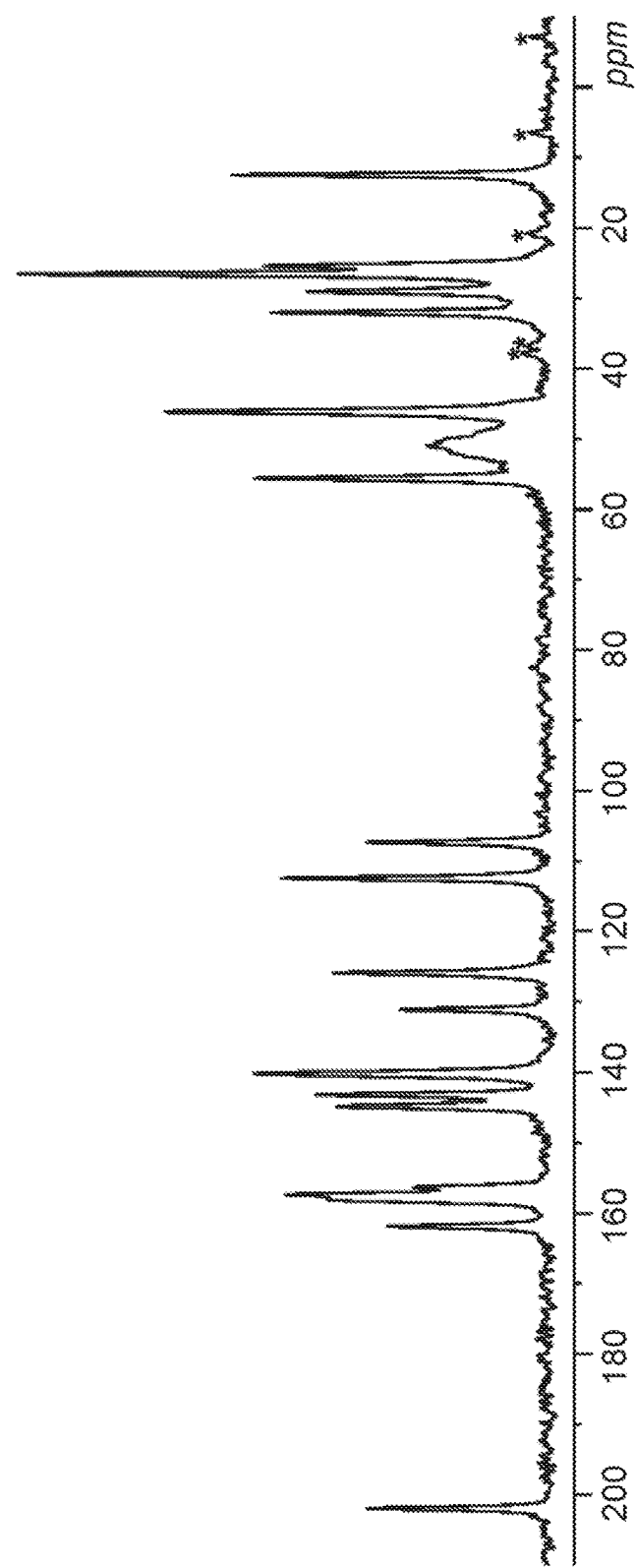
FIG. 2 shows the Carbon CPMAS spectrum of compound 1 free base, polymorph Form A. Peaks marked by asterisks are spinning sidebands.

The solid state nuclear magnetic resonance (ssNMR) for crystalline free base Form A of compound 1 is shown in FIG. 2 and the corresponding data is tabulated in Table 2.

TABLE 2

$^{13}$C chemical shifts in parts per million for polymorph Form A of compound 1.
$^{13}$C Chemical Shifts
[ppm]$^a$ ± 0.2

| |
|---|
| 12.50 |
| 25.40 |
| 26.54 |
| 29.04 |
| 32.03 |
| 46.15 |
| 51.01 |
| 55.66 |
| 107.34 |
| 112.44 |
| 125.94 |
| 131.14 |
| 140.15 |
| 143.15 |
| 144.85 |
| 156.32 |
| 157.35 |
| 158.06 |
| 161.88 |
| 201.94 |

$^a$Referenced to external sample of solid phase adamantane at 29.5 ppm.

Figure 3:
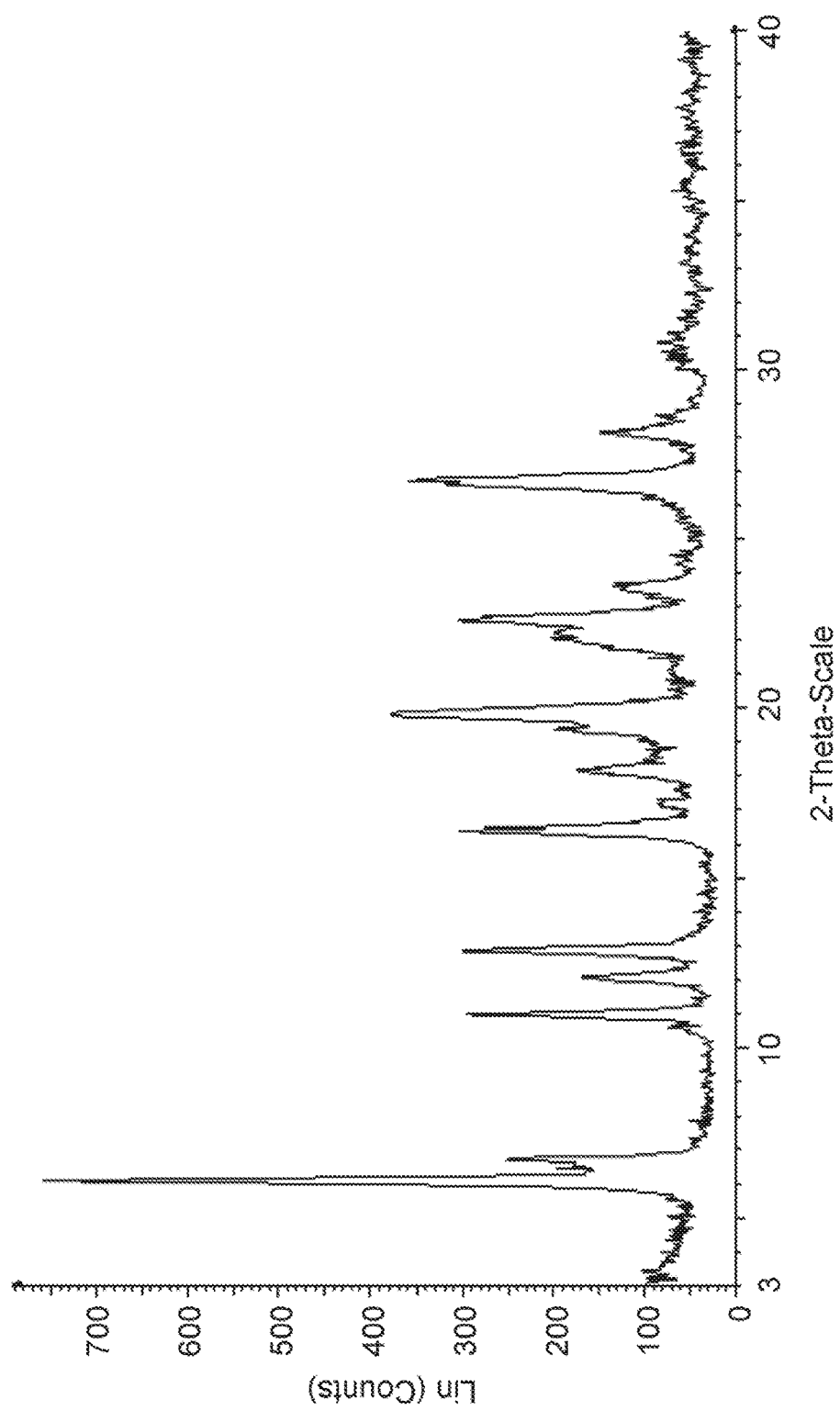
FIG. 3 shows a PXRD pattern of compound 1 free base, polymorph Form B.

In another aspect, the invention provides a crystalline free base of compound 1, wherein the crystalline free base is a polymorph Form B of the free base of compound 1. In some embodiments of this aspect, the crystalline form has a powder X-ray diffraction pattern comprising a peak at diffraction angle (2θ) of 6.0±0.2. In other embodiments of this aspect, the crystalline form has a powder X-ray diffraction pattern comprising peaks at diffraction angles (2θ) of 6.0±0.2 and 19.8±0.2. In further embodiments of this aspect, the crystalline form has a powder X-ray diffraction pattern comprising peaks at diffraction angles (2θ) of 6.0±0.2, 19.8±0.2, and 26.7±0.2. In further embodiments, the crystalline form has a powder X-ray diffraction pattern comprising peaks at diffraction angles (2θ) of 6.0±0.2, 16.4±0.2, 19.8±0.2, and 26.7±0.2. In still other embodiments, the crystalline form has a powder X-ray diffraction pattern comprising peaks at diffraction angles (2θ) of 6.0±0.2, 12.8±0.2, 16.4±0.2, 19.8±0.2, and 26.7±0.2. In additional embodiments, the crystalline form has a powder X-ray diffraction pattern comprising peaks at diffraction angles (2θ) of 6.0±0.2, 12.8±0.2, 16.4±0.2, 19.8±0.2, 22.6±0.2, and 26.7±0.2. In yet other embodiments, the crystalline form has a powder X-ray diffraction pattern comprising peaks at diffraction angles (2θ) of 6.0±0.2, 10.9±0.2, 12.8±0.2, 16.4±0.2, 19.8±0.2, 22.6±0.2, and 26.7±0.2. In some embodiments of this aspect, the crystalline form has a PXRD pattern comprising peaks at diffraction angles (2θ) essentially the same as shown in FIG. 3. The powder X-ray diffraction (PXRD) pattern of free base polymorph Form B is shown in FIG. 3 and the corresponding data is tabulated in Table 3.

TABLE 3

PXRD data for polymorph Form B of compound 1.

| 2θ (°) ± 0.2 | Peak Intensity (%) |
|---|---|
| 6.0 | 100 |
| 10.9 | 39 |
| 12.8 | 40 |
| 16.4 | 41 |
| 19.8 | 50 |
| 18.1 | 24 |
| 12.1 | 23 |
| 22.6 | 40 |
| 26.7 | 48 |
| 28.2 | 20 |

Figure 4:
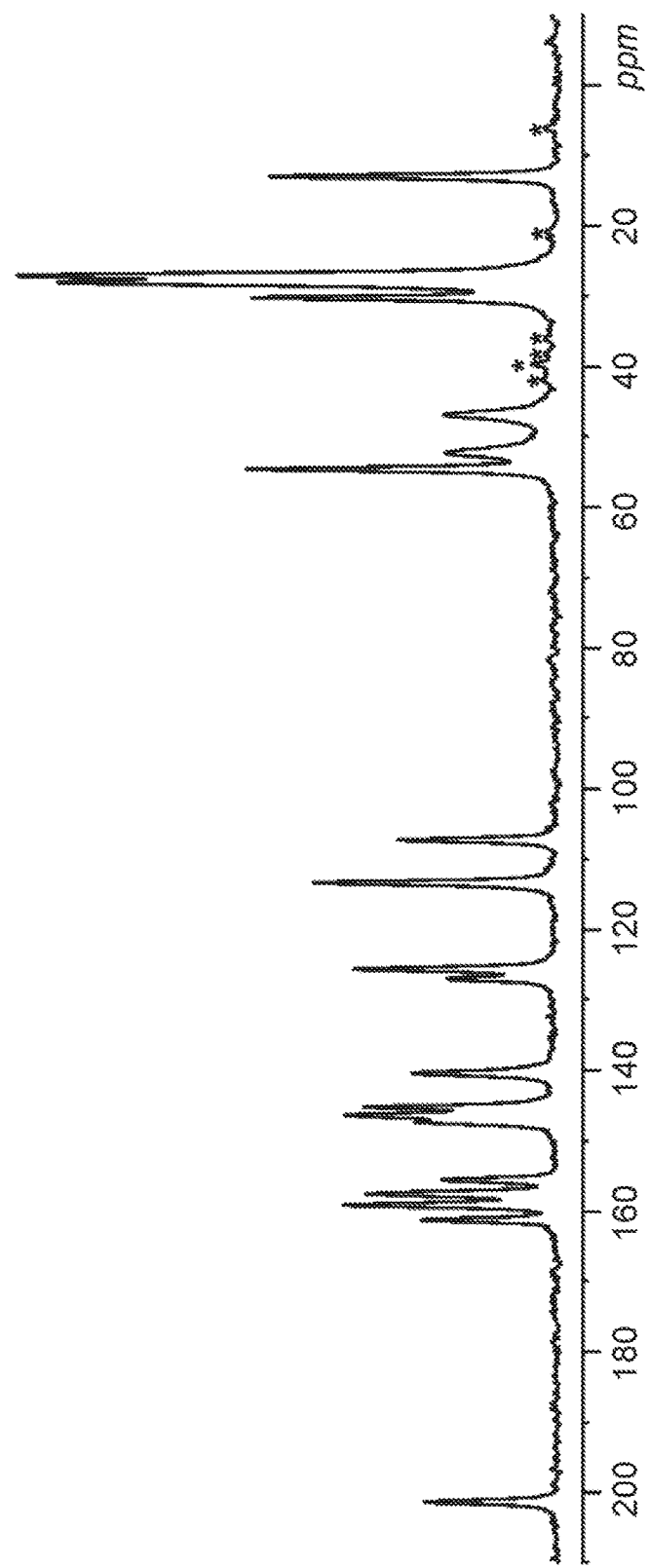
FIG. 4 shows the Carbon CPMAS spectrum of compound 1 free base, polymorph Form B. Peaks marked by asterisks are spinning sidebands.

The solid state nuclear magnetic resonance (ssNMR) for crystalline free base Form B of 6-acetyl-8-cyclopentyl-5-methyl-2-(5-piperazin-1-yl-pyridin-2-ylamino)-8H-pyrido[2,3-d]pyrimidin-7-one is shown in FIG. 4, with corresponding tabulated data shown in Table 4.

TABLE 4

$^{13}$C chemical shifts in parts per million for polymorph Form B of compound 1.

| $^{13}$C Chemical Shifts [ppm]$^a$ ± 0.2 |
|---|
| 13.06 |
| 27.10 |
| 28.04 |
| 30.23 |
| 46.90$^b$ |
| 52.32$^b$ |
| 54.63 |
| 107.28 |
| 113.35 |
| 125.67 |
| 127.04 |
| 140.40 |
| 145.21 |
| 146.37 |
| 147.34 |
| 155.57 |
| 157.59 |
| 159.18 |
| 161.29 |
| 201.35 |

$^a$Referenced to external sample of solid phase adamantane at 29.5 ppm.
$^b$Broad peak For each powder X-ray diffraction measurement, a sample of a free base was placed into a cavity located on a planar surface of the holder, and a glass slide was used to level the surface of the sample. The holder, which contains the sample, was placed in the diffractometer, and the source of the X-ray beam irradiated the sample, initially at a small angle relative to the planar surface of the holder. The X-ray beam was subsequently moved through an arc in a step-wise manner, which successively increased the angle between the incident beam and the planar surface of the holder. At each step of the scan, the scintillation counter detected the amount of diffracted radiation, which was recorded as a function of 2θ (°). The instrument software displays the diffracted radiation results of the scan as intensity versus 2θ (°).

Tables 1 and 3 list significant PXRD peaks (i.e., those exhibiting peak height to noise ratio greater than 3.5) for the free base of compound 1 having polymorph Form A or Form B, respectively. The list of characteristic peaks provided is not the only possible list of characteristic peaks. Persons of ordinary skill in the art of polymorph identification may choose other sets of characteristic peaks that will also distinguish one polymorph from another.

Differences in PXRD patterns among separate measurements of the same polymorph may arise for many reasons. Sources of error include variations in sample preparation (e.g. sample height), instrument errors, calibration errors, and operator errors (including errors in determining peak locations). Preferential orientation, i.e., a lack of random orientation of crystals in the PXRD sample, can result in significant differences in relative peak heights. Calibration errors and sample height errors often result in a shift of all of the peaks of the diffractogram in the same direction and by the same amount. Small differences in sample height on a flat holder may lead to large displacements in PXRD peak positions. For a systematic study showing that sample height differences of 1 mm may lead to peak shifts as high as 1° 2θ, see Chen et al., *J. Pharmaceutical and Biomedical Analysis* (2001) 26:63.

In many instances, peak shifts among diffraction patterns resulting from systematic error can be eliminated by compensating for the shift (e.g., applying a correction factor to all peak position values) or by recalibrating the diffractometer. Generally, the same techniques can be used to compensate for differences among diffractometers so that PXRD peak positions obtained from two different instruments can be brought into agreement. Furthermore, when these techniques are applied to PXRD measurements from the same or different diffractometers, the peak positions for a particular polymorph will usually agree to within about ±0.20 2θ.

The disclosed compounds embrace all pharmaceutically acceptable isotopic variations. An isotopic variation is a compound in which at least one atom is replaced by an atom having the same atomic number, but an atomic mass different from the atomic mass usually found in nature. Useful isotopes include isotopes of hydrogen, carbon, nitrogen, oxygen, phosphorus, sulfur, fluorine, and chlorine. Exemplary isotopes thus include, without limitation, $^2$H, $^3$H, $^{13}$C, $^{14}$C, $^{15}$N, $^{17}$O, $^{18}$O, $^{32}$P, $^{35}$S, $^{18}$F, and $^{36}$Cl.

Substitution of the disclosed compounds with isotopes such as deuterium, i.e. $^2$H, may afford certain therapeutic advantages resulting from greater metabolic stability, for example, increased in vivo half-life or reduced dosage requirements, and hence may be more useful in some circumstances. In addition, certain isotopic variations, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Isotopic variations of the disclosed compounds can generally be prepared by conventional techniques known to those skilled in the art or by processes analogous to those described in the accompanying Examples using appropriate isotopic variations of suitable reagents. Pharmaceutically acceptable solvates of the disclosed compounds include those in which the solvent of crystallization may be isotopically substituted, e.g. $D_2O$, $d_6$-acetone, $d_6$-DMSO.

Solubility Experiments

U.S. Pat. No. 7,345,171 reported that the free base of compound 1, prepared by a traditional salt break procedure, had poor water solubility (9 μg/mL) at pH 7.9 and exhibited low bioavailability in animal studies. The free base was reported to be in its most stable crystal phase according to slurry experiments (i.e., Form A). FIG. 17 of U.S. Pat. No. 7,345,171 provided the water adsorption/desorption isotherms for the free base of Form A. As noted previously, this material corresponds to the small particle size free base of compound 1 described herein.

The free base of compound 1 (Form A) has a high propensity for punch sticking in the drug particle manufacturing process. As punch sticking is related to API surface area, API particle size control is critical for minimizing sticking during drug product manufacturing. In addition to issues with punch sticking, compound 1 free base isolated directly from a standard salt break process was found to be highly static prone and found to form large (approximately 500 microns) hard agglomerates that were not dispersed by sieving. Free base API with similarly poor physical properties was produced by free basing of the existing isethionate salt API or by neutralization of the in situ salt formed in the final step of the API synthesis. In either process, small API primary particles were produced due to the rapid crystallization caused by the dramatic change in solubility with adjustment of the pH. In all cases the free base was isolated as the more stable polymorph of Form A.

Figure 6:
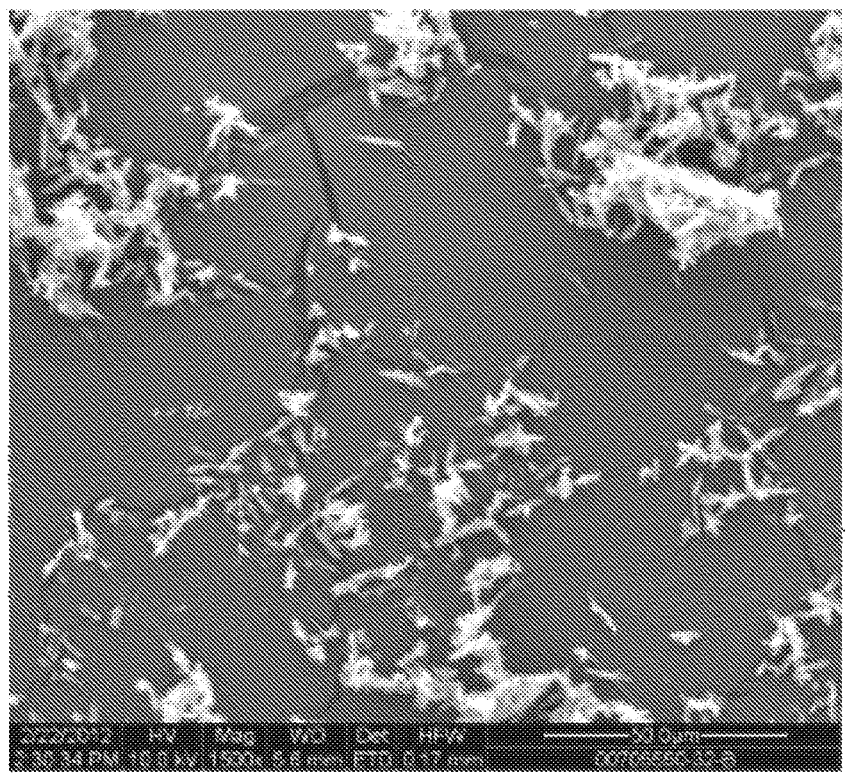
FIG. 6 shows a scanning electron microscopy (1500× magnification) image of compound 1 free base API, polymorph Form A, isolated from a standard free basing process.
Figure 8:
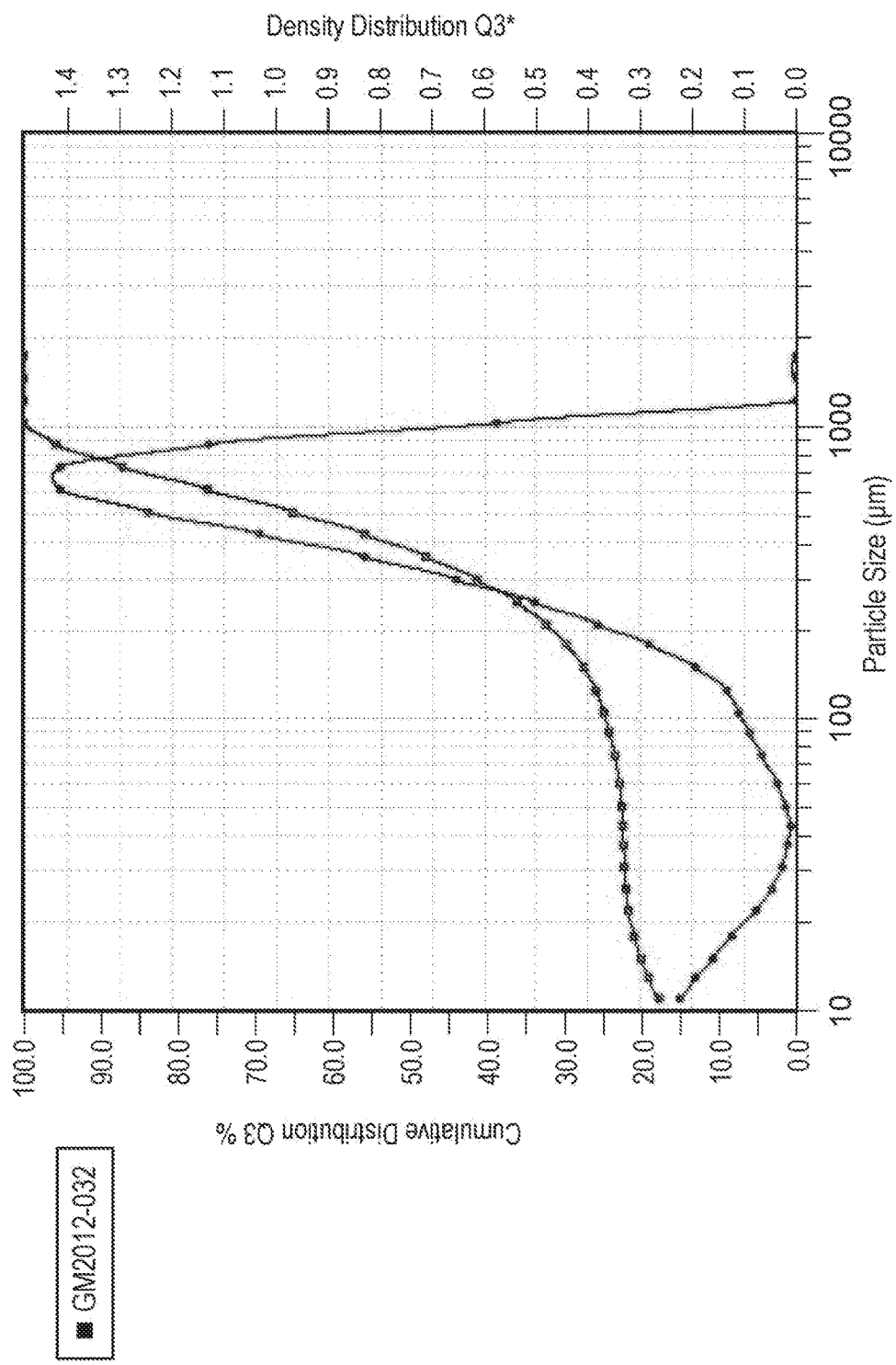
FIG. 8 shows the particle size distribution of compound 1 free base API, polymorph Form A, isolated from a standard free basing process.

FIG. 6 shows a scanning electron microscopy (SEM) image of typical small primary particles formed by the free basing and neutralization experiments described above. The particle size distribution measurement for a batch of compound 1 (Form A) produced by this free base isolation process is provided in FIG. 8. The second mode in the particle size distribution was caused by the presence of large agglomerates, which are also seen in the SEM image in FIG. 6. Attempts to modify the free basing process were not successful in improving the physical properties of the API produced. As the process for producing free base resulted in the isolation of API with poor physical properties, work was undertaken to identify a recrystallization process that could improve the API physical properties.

Early crystallization screening experiments for compound 1 free base were completed to identify a solvent system that allows for the isolation of particles with improved physical properties. A combination of solubility screening and small-scale recrystallization studies examined multiple potential solvent systems.

Small-Scale Crystallization Studies

A series of small-scale crystallization experiments was run to identify a potential recrystallization solvent system as well as to assess the impact of solvent on the shape of the free base primary particles isolated. An initial set of 14 screening studies were run on a 10 mg scale using sealed vials and an external heat source to warm the 50 mg/mL samples up to reflux temperature. Visual observation identified the samples that went into solution, and photomicroscopy was used to characterize the particles produced. The results of these initial crystallization screening experiments are summarized in Table 5.

TABLE 5

Summary of results from preliminary small scale crystallization studies

| Solvent System | Results of recrystallization |
| --- | --- |
| Cyclopentylmethyl ether | did not dissolve |
| n-Butyl Acetate | did not dissolve |
| n-Butanol | did not dissolve |
| Trifluorotoluene | did not dissolve |
| Toluene | did not dissolve |
| Chlorobenzene | small irregular shaped particles |
| DMF | small needle shaped particles |
| NMP | small irregular shaped particles |
| Propylene glycol | small irregular shaped particles |
| Anisole | large particles (lathes or tomahawk shape) |
| Pyridine | small lathe shaped particles |
| Sulfolane | small irregular shaped particles |
| m-Xylene | small/medium tomahawk shaped particles |
| Mesitylene | small needle shaped particles |

Based on these small-scale crystallization studies, anisole became the focus of additional crystallization and solubility studies as the particles produced were large and as anisole is an ICH Class III solvent. This screening study also identified pyridine, m-xylene, and mesitylene as potential solvent systems based on the particles produced, although none of these solvents also have the ICH class III listing similar to anisole.

The following solvents have also been used for recrystallization of the solid: isopropanol, isobutanol, ethanol, ethyl acetate, toluene, tetrahydrofuran, and dioxane. Each of the solvents generated the polymorph Form A crystalline solid of compound 1 which was the same as the original crystalline form obtained from dichloromethane.

Solubility Studies:

In parallel with the initial small-scale crystallization studies, a series of solubility studies were conducted on the free base of compound 1 to identify a possible recrystallization system. In an initial room temperature solubility screening study, a total of 23 solvents were screened. This study indicated that the compound 1 free-base has low solubility in a range of organic solvents, with only methylene chloride displaying a solubility greater than 1 mg/mL (3.0 mg/mL). Subsequent targeted higher temperature solubility studies were conducted. In a follow-up study, a set of 16 solvent systems were examined at a fixed concentration of 25 mg/mL, and the dissolution temperature was measured using a kinetic solubility method up to a maximum temperature of 110° C.

Synergistic solubility behavior predicted by a COSMO-therm solubility model of compound 1 was used to select the binary and ternary solvent systems included in this screening study. The results of these studies are listed in Table 6. For experiments listed as >110° C. in the table, compound 1 did not dissolve in the solvent upon heating to 110° C., indicating that the solubility is less than 25 mg/mL at 110° C. in this solvent.

TABLE 6

Kinetic solubility measurements for 25 mg/mL compound 1 free base solutions

| Experiment # | Solvent | Dissolution Temp. (° C.) |
| --- | --- | --- |
| 1 | n-BuOH | >110° C. |
| 2 | DMF | >110° C. |
| 3 | NMP | 97.9 |
| 4 | DMSO | >110° C. |

TABLE 6-continued

Kinetic solubility measurements for 25 mg/mL compound 1 free base solutions

| Experiment # | Solvent | Dissolution Temp. (° C.) |
|---|---|---|
| 5 | DMAc | >110° C. |
| 6 | n-Butyl acetate | >110° C. |
| 7 | Anisole | >110° C. |
| 8 | 10% n-BuOH/Anisole (v/v) | >110° C. |
| 9 | 20% n-BuOH/Anisole (v/v) | 109.7 |
| 10 | 40% n-BuOH/Anisole (v/v) | 101.4 |
| 11 | 10% n-BuOH/NMP (v/v) | 103.7 |
| 12 | 25% n-BuOH/NMP (v/v) | >110° C. |
| 13 | 10% 1,4-butanediol/anisole (v/v) | 109.8 |
| 14 | 25% 1,4-butanediol/anisole (v/v) | 104.8 |
| 15 | 1:1:8 propylene glycol/n-BuOH/anisole (v/v) | 91.2 |
| 16 | 2:1:7 propylene glycol/n-BuOH/anisole (v/v) | 84.1 |

Subsequent UPLC/MS testing of the saturated solution from experiments #3 and #11 in Table 6 indicated the presence of a previously unseen impurity peak, indicating that degradation occurred in these experiments.

Although the propylene glycol/n-BuOH/anisole mixtures showed improved solubility as compared to the n-BuOH/anisole mixtures, the former solvent system was not pursued because of the potential challenges of working with propylene glycol due to its high viscosity and boiling point which may cause issues on-scale.

Based on these screening studies, a mixture of 40% n-butanol and anisole was selected as the crystallization solvent system for further work, in view of the relatively high solubility, chemical stability of the API, and particle properties of the recrystallized compound 1 API. This solvent system was used in subsequent production to provide larger primary particle size API that had reduced sticking, was not static prone, and was free of agglomerates.

Figure 7:
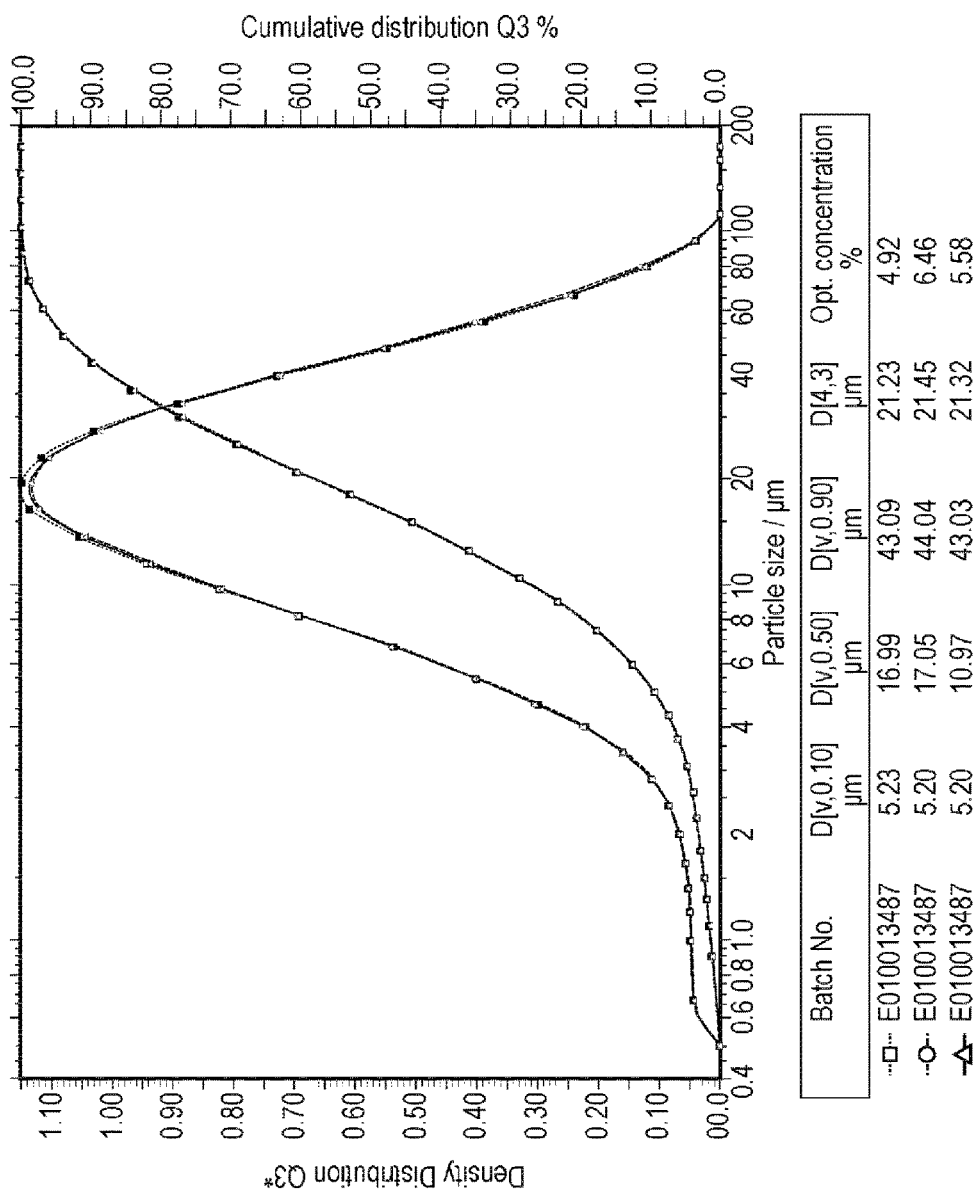
FIG. 7 shows the particle size distribution of compound 1 free base API, polymorph Form A, recrystallized from 40% n-BuOH/anisole.
Figure 9:
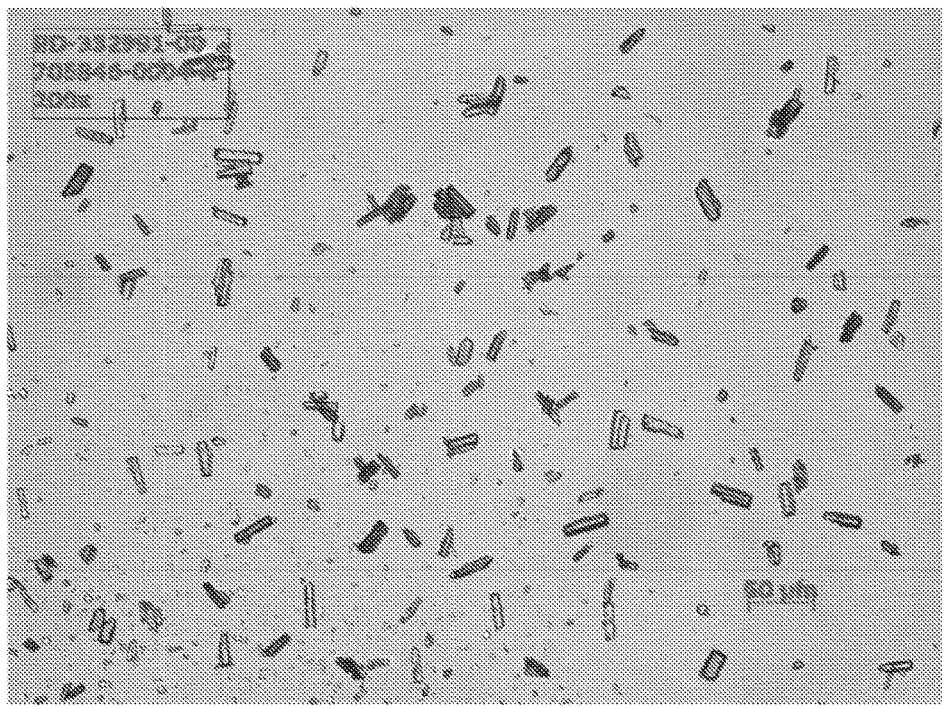
FIG. 9 shows a polarized light microscopy (PLM) image (200×) of compound 1 free base API, polymorph Form A, recrystallized from 40% n-BuOH/anisole.

Using this solvent mixture, compound 1 was dissolved with 40 mL/g of solvent (concentration of 25 mg/mL) by heating to 95-100° C., before being crystallized using a controlled cooling profile and seeding to induce nucleation. FIG. 9 is a PLM image of a lab-scale lot of compound 1 recrystallized using this recrystallization procedure, while FIG. 7 displays a particle size distribution for three lots of recrystallized API. This recrystallization process results in the isolation of compound 1 API particles with a larger primary particle size, which leads to a decrease in the sticking tendency in the drug product manufacturing process. This recrystallized compound 1 API does not form agglomerates and also has the positive attribute of not being static prone.

The combination of solubility screening and small-scale recrystallization studies examined multiple potential solvent systems for the recrystallization of compound 1 free base. Based on the results from these screening studies, a mixture of 40% n-butanol/anisole was selected as the preferred crystallization solvent system based on the relatively high solubility, chemical stability of the API, and particle properties of the recrystallized compound 1. The larger particle size and improved particle properties of the API isolated from this recrystallization process facilitated the development of a drug product manufacturing process for compound 1 free base.

Particle Size Assessment

Particle sizes for the recrystallized materials were assessed using laser diffraction methods. Laser diffraction is recognized by standards and guidance agencies including ISO and ASTM and is widely used to determine particle size distributions. In conducting the assessment, the sample is passed through a laser beam which results in laser light scattered at a range of angles. Detectors placed at fixed angles measure the intensity of light scattered at that position. A mathematical model (Mie or Fraunhoffer Theory) is then applied to generate a particle size distribution.

The particle size was analyzed using the laser diffraction (or small angle light scattering) technique by dispersing the dry sample powder with compressed air. Specifically, the particle size distribution was analyzed using the Sympatec HELOS RODOS system equipped with a Vibri dry powder feeder. The powder sample was dispersed with a dispersion pressure of 0.5 bar. In some instances, an Aspiros micro-dosing device was used, and the powder sample was dispersed with a dispersion pressure of 0.2 bar. A suitable lens was selected to cover the particle size range of each sample.

In particle size determinations, the median value is defined as the value where half of the population resides above this point, and half resides below this point. For particle size distributions the median is called the D50. The D50 is the size in microns that splits the distribution with half above and half below this diameter. The expression Dv50 or D[v,0.5] is sometimes used for the median of a volume distribution.

The mode is the peak of a frequency distribution. A particle distribution may include more than one mode, e.g., where the particles exist as primary particles and agglomerations.

The span is sometimes used as a measurement of distribution width, and is defined as the ratio of (D[v,0.9]–D[v,0.1])/D[v,0.5] or (D90–D10)/D50.

The distribution width may also be characterized by citing one, two or preferably three values on the x-axis, typically some combination of the D10, D50, and D90. The D50, the median, has been defined above as the diameter where half of the population lies below this value. Similarly, 90 percent of the distribution lies below the D90, and 10 percent of the population lies below the D10.

The term D[4,3] refers to the volume mean or mass moment mean. Laser diffraction results are reported on a volume basis and the volume mean can be used to define the central point of the distribution. The D[4,3] value is sensitive to the presence of large particles in the distribution.

Formulation

The present invention also relates to pharmaceutical compositions comprising the free base polymorph Form A of compound 1 described herein. Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Reminqton's Pharmaceutical Sciences*, Mack Publishing Company, Easter, Pa., 15th Edition (1975).

The disclosed compound may be administered alone or in combination with other drugs and will generally be administered as a formulation in association with one or more pharmaceutically acceptable excipients. The term "excipient" describes any ingredient other than compound 1 and its salts. The choice of excipient will to a large extent depend on the particular mode of administration.

The disclosed compounds may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations. Liquid formulations include suspensions, solutions, syrups and elixirs. Such formulations may be employed as fillers in soft or hard capsules and typically comprise a carrier, for example, water, EtOH, polyethylene glycol, propylene glycol, methylcellulose, or a suitable oil, and one or more emulsifying agents and/or suspending agents. Liquid formulations may also be prepared by the reconstitution of a solid, for example, from a sachet.

The disclosed compounds may also be used in fast-dissolving, fast-disintegrating dosage forms such as those described in Liang and Chen, *Expert Opinion in Therapeutic Patents* (2001) 11(6):981-986.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch, and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose, and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally include surface-active agents, such as sodium lauryl sulfate and polysorbate 80, and glidants such as silicon dioxide and talc. When present, surface-active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 wt % to 10 wt %, preferably from 0.5 wt % to 3 wt % of the tablet. Other ingredients may include preservatives, antioxidants, flavors, and colorants.

Tablet blends may be directly compressed to form tablets. Tablet blends or portions of blends may alternatively be wet-, dry-, or melt-granulated, melt congealed, or extruded before tabletting. The final formulation may comprise one or more layers and may be coated or uncoated. Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant. For additional details concerning the formulation of tablets, see H. Lieberman and L. Lachman, *Pharmaceutical Dosage Forms: Tablets, Vol.* 1 (1980).

Solid formulations for oral administration may be formulated to be immediate and/or modified release. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14. For a discussion of the use of chewing gum to achieve controlled release, see WO 00/35298.

The disclosed compounds may also be administered directly into the blood stream, into muscle, or into an internal organ. Suitable means for parenteral administration include intravenous, intra-arterial, intraperitoneal, intrathecal, intraventricular, intraurethral, intrasternal, intracranial, intramuscular, and subcutaneous. Suitable devices for parenteral administration include needle (including microneedle) injectors, needle-free injectors and infusion techniques.

Parenteral formulations are typically aqueous solutions which may contain excipients such as salts, carbohydrates, and buffering agents (preferably to a pH of from 3 to 9), but for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Exemplary parenteral administration forms include solutions or suspensions of active compounds in sterile aqueous solutions, for example, aqueous propylene glycol or dextrose solutions. Such dosage forms can be suitably buffered, if desired.

The solubility of the disclosed compounds used in the preparation of parenteral solutions may be increased by the use of appropriate formulation techniques, such as the incorporation of solubility-enhancing agents. Formulations for parenteral administration may be formulated to be immediate and/or modified release as described above. Thus the disclosed compounds may be formulated in a more solid form for administration as an implanted depot providing long-term release of the active compound.

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol and propylene glycol. Topical formulations may also include penetration enhancers. See, for example, Finnin and Morgan, *J Pharm Sci* (1999) 88(10):955-958.

Other means of topical administration include delivery by iontophoresis, electroporation, phonophoresis, sonophoresis and needle-free (e.g. POWDERJECT) or micro-needle injection. Formulations for topical administration may be formulated to be immediate and/or modified release as described above.

The disclosed compounds can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulizer, with or without the use of a suitable propellant, such as dichlorofluoromethane. The pressurized container, pump, spray, atomizer, or nebulizer contains a solution or suspension, which comprises the active compound, an agent for dispersing, solubilizing, or extending release of the active compound (e.g., EtOH or aqueous EtOH), one or more solvents, which serve as a propellant, and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules, blisters and cartridges (made, for example, from gelatin or hydroxypropylmethyl cellulose) for use in an inhaler or insufflator may be formulated to contain a powder mix of the active compound, a suitable powder base such as lactose or starch, and a performance modifier such as L-leucine, mannitol, or magnesium stearate. The lactose may be anhydrous or, preferably, monohydrated. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µl to 100 µl. A typical formulation may comprise compound 1, propylene glycol, sterile water, EtOH, and NaCl. Alternative solvents, which may be used instead of propylene glycol, include glycerol and polyethylene glycol.

Formulations for inhaled/intranasal administration may be formulated to be immediate and/or modified release using, for example, poly(DL-lactic-coglycolic acid (PGLA). Suitable flavors, such as menthol and levomenthol, or sweeteners, such as saccharin or saccharin sodium, may be added to formulations intended for inhaled/intranasal administration.

In the case of dry powder inhalers and aerosols, the dosage unit is determined by means of a valve that delivers a metered amount. Units in accordance with the invention are typically arranged to administer a metered dose or "puff" containing from 100 to 1000 µg of the active pharmaceutical ingredient. The overall daily dose will typically be in the range 100 µg to 10 mg which may be administered in a single dose or, more usually, as divided doses throughout the day.

The active compounds may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release as described above.

The disclosed compounds may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer (e.g., hydroxypropylmethylcellulose, hydroxyethylcellulose, or methyl cellulose), or a heteropolysaccharide polymer (e.g., gelan gum), may be incorporated together with a preservative, such as benzalkonium chloride. Such formulations may also be delivered by iontophoresis. Formulations for ocular/andial administration may be formulated to be immediate and/or modified release as described above.

The disclosed compounds may be combined with soluble macromolecular entities such as cyclodextrin or polyethylene glycol-containing polymers to improve their solubility, dissolution rate, taste masking, bioavailability and/or stability. Drug-cyclodextrin complexes, for example, are found to be generally useful for most dosage forms and administration routes. Both inclusion and non-inclusion-complexes may be used. As an alternative to direct complexation with the drug, the cyclodextrin may be used as an auxiliary additive, i.e. as a carrier, diluent, or solubilizer. Alpha-, beta- and gamma-cyclodextrins are commonly used for these purposes. See, for example, International Patent Applications WO 91/11172, WO 94/02518, and WO 98/55148.

The therapeutically effective dose of compound 1 will vary from approximately 0.01 mg/kg to approximately 100 mg/kg of body weight per day. Typical adult doses will be approximately 0.1 mg to approximately 3000 mg per day. The quantity of active component in a unit dose preparation may be varied or adjusted from approximately 0.1 mg to approximately 500 mg, preferably from about 0.6 mg to 100 mg according to the particular application and the potency of the active component. The composition can, if desired, also contain other compatible therapeutic agents. A subject in need of treatment is administered a dosage of about 0.6 to about 500 mg per day, either singly or in multiple doses over a 24-hour period. Such treatment may be repeated at successive intervals for as long as necessary.

Disorders or conditions caused by abnormal cell proliferation include cancer and vascular smooth muscle proliferation associated with atherosclerosis, post-surgical vascular stenosis and restenosis, and endometriosis. Autoimmune diseases include psoriasis, inflammation-like rheumatoid arthritis, lupus, type 1 diabetes, diabetic nephropathy, multiple sclerosis, glomerulonephritis, and organ transplant rejection, including host versus graft disease.

In one embodiment, the present invention provides a method of treating abnormal cell growth in a mammal, including a human, in need of such treatment comprising, administering to said mammal a therapeutically effective amount of a crystalline free base of compound 1 according to the invention described herein. In frequent embodiments, the free base is a polymorph of Form A.

In another embodiment, the abnormal cell growth is cancer, including both solid tumors and hematological malignancies. In some such embodiments, the cancer is selected from breast cancer, ovarian cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma).

General Synthetic Scheme

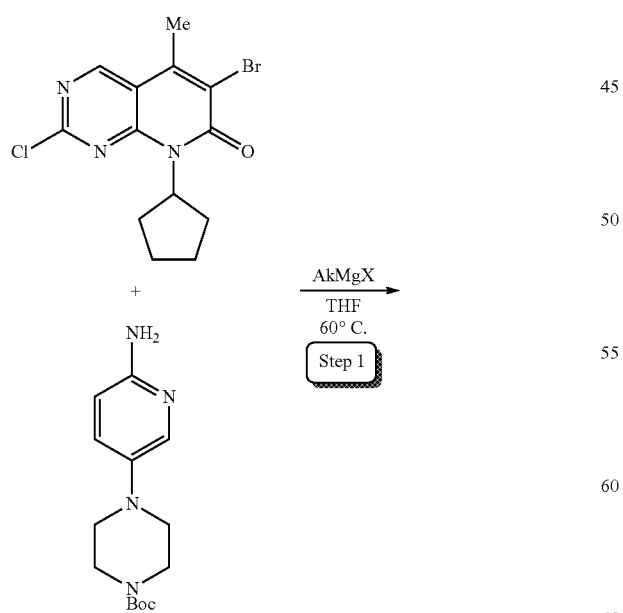

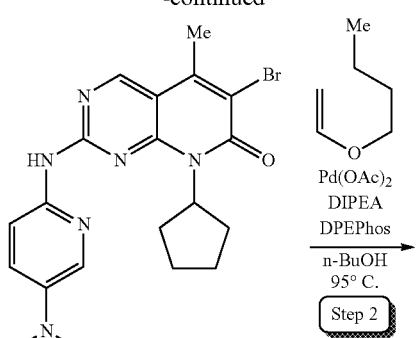

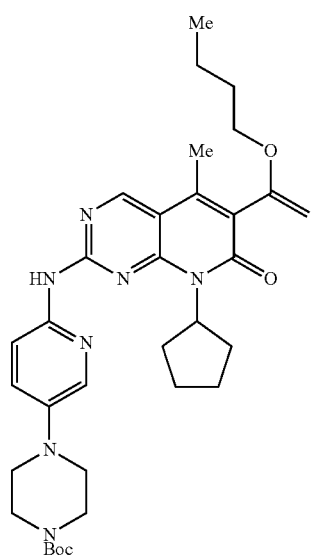

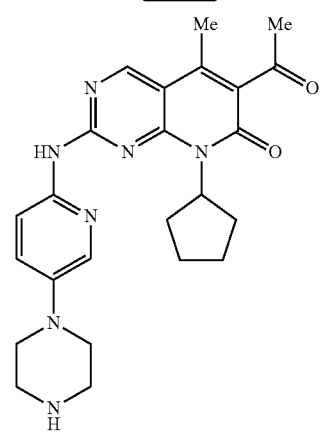

The examples and preparations provided below further illustrate and exemplify particular aspects of embodiments of the invention. It is to be understood that the scope of the present invention is not limited in any way by the scope of the following examples.

EXAMPLES

General Methods and Materials
Powder X-Ray Diffraction (PXRD)

PXRD data were collected according to the following protocol. A sample (2 mg) was placed on a microscopic slide with zero background. The sample was then placed in a Discover D8 (Bruker AXS Instruments) equipped with a GADDS detector. The system used a copper X-ray source maintained at 40 kV and 40 mA to provide CUα1 emission at 1.5406 angstroms. Data were collected from 4 to 40° 2θ using a step scan of 0.02° with a step time of 60.1 seconds. Diffraction peaks are typically measured with an error of ±0.2 degrees (2θ).

SSNMR Instrumentation and Method

SSNMR data were collected according to the following protocol. Spectra were collected on Bruker-Biospin 4 mm and 7 mm BL CPMAS probe positioned into a wide-bore Bruker-Biospin Avance III 500 MHz NMR spectrometer. The 4 mm rotors were oriented at the magic angle and spun at 15.0 kHz. The 7 mm rotors were oriented at the magic angle and spun at 7.0 kHz. All spectra were acquired at ambient conditions (temperature uncontrolled).

The $^{13}$C solid state spectra were collected using a proton decoupled cross-polarization magic angle spinning (CP-MAS) experiment. Peak resonances are reported in parts-per-million (ppm)±0.2 ppm.

Differential Scanning Calorimetery (DSC):

DSC measurements, are carried out using a Q1000, Thermal Analysis Instruments. A sample is placed in a hermetically sealed aluminum pan with a pinhole. A typical sample weight is 1.6 mg. The sample is equilibrated to 25° C. and then ramped to 250° C. at a scan rate of 10° C./min. Dry nitrogen is used as the purge gas.

Brunauer, Emmet and Teller (BET) Specific Surface Area (SSA) Measurement:

SSA measurements were collected according to the following protocol. Monolayer formation of gas molecules on the crystal surface was used to determine the specific surface area of a dry powder of active pharmaceutical ingredient. The sample was made free of moisture and atmospheric vapours by applying heat and purging with nitrogen gas. The sample temperature was then reduced to that of liquid nitrogen for the adsorbate gas (nitrogen) to be adsorbed. The quantity of adsorbed gas and pressure data were used to generate an adsorption isotherm plot. The data were then converted into specific surface area value using a mathematical algorithm based on the so-called Brunauer, Emmett, and Teller (BET) theory (see, e.g., *J. Am. Chem. Soc.*, 1938, 60:309). Specific surface area was measured using a static multi-point or single-point gas adsorption method, as fully described in ISO 9277:2010 and in the experimental below.

Inverse-Phase Gas Chromatography (IGC) Surface Energy Measurement:

Surface energy measurements were collected using IGC according to the following protocol. A sufficient quantity of sample was packed into a silanised glass column with the powder mass secured within the column by glass wool plugs inserted at both ends. The column was conditioned by flowing a stream of dry nitrogen through the powder mass for sufficient time for any surface adsorbates to be removed. Measurements were made by injecting a series of alkane vapour probes (Nonane, Octane, Heptane and Hexane) into the carrier gas stream at concentrations low enough to assume infinite dilution of the alkane vapour in the nitrogen stream and recording the time taken for each vapour to elute through the column. A plot of the retention time (corrected for the 'dead volume' of interstitial space within the packed column) versus a function of the cross sectional area and surface tension of the alkane vapour probe molecules used yielded a line with a slope indicative of the surface energy of the solid powder under examination.

SYNTHETIC EXAMPLES

Example 1. Preparation of 4-(6-amino-pyridin-3-yl)piperazine-1-carboxylic acid tert-butyl ester

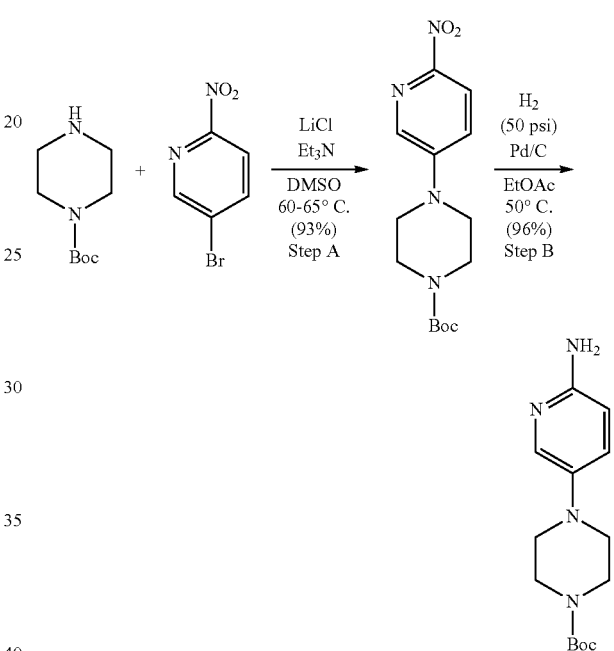

Step A. Preparation of 4-(6-nitro-pyridin-3-yl)-piperazine-1-carboxylic acid tert-butyl ester To a vessel was added 5-bromo-2-nitropyridine (10.0 g, 1.0 equiv.) along with DMSO (25 mL, 2.5 vol). N-Boc piperazine (13.8 g, 1.5 equiv.) was added, followed by triethylamine (7.5 g, 1.5 equiv.) and LiCl (2.1 g, 1.0 equiv.). The mixture was warmed to 60-65° C. for a minimum of 12 hours.

Water (5 mL, 0.5 vol) was added slowly to the vessel at 60-65° C. The mixture was kept at 60-65° C. for one hour, then cooled to room temperature. The slurry was kept at 20-25° C. for 1 hour and then filtered onto a #2 Whatman™ paper filter. The cake was rinsed with water (50 mL, 5 vol.). The crude solids were collected and transferred back to a clean vessel.

Water (100 mL, 10 vol.) was added to the vessel containing the solids and the mixture was warmed to 35-40° C. for 2 hours, then filtered while warm onto a #2 Whatman Paper™ filter. The solids were rinsed with water (40 mL, 4 vol.) and allowed to dry overnight in the vacuum oven at 50-55° C. The 4-(6-nitro-pyridin-3-yl)-piperazine-1-carboxylic acid tert-butyl ester was isolated as a yellow solid (14.1 g collected; ~93% yield).

Step B. Preparation of 4-(6-amino-pyridin-3-yl)-piperazine-1-carboxylic acid tert-butyl ester To a vessel was added 4-(6-nitro-pyridin-3-yl)-piperazine-1-carboxylic acid tert-butyl ester (12.0 g, 1.0 equiv.) along with ethyl acetate (48 mL, 4.0 vol.). To the slurry was added 50% water wet 5% Pd/C (480 mg, 4% w/w) and the vessel was purged three times with nitrogen. The vessel was purged three times with hydrogen and then pressurized to 50 psi hydrogen. The mixture was heated to 42-47° C. and allowed to stir until hydrogen uptake ceased (at least 8 hours).

The product mixture was filtered and washed with ethyl acetate (2×1.5 mL). The combined filtrate was concentrated under reduced pressure to a volume of 6 mL (2 vol.). To the solution was added n-heptane (54 mL, 4.5 vol.) and the mixture was distilled under reduced pressure to a volume of 6 mL (2 vol.). To the solution was added n-heptane (54 mL, 4.5 vol.). The resulting thick slurry was cooled to 20-25° C. and allowed to stir for 2 hours. The slurry was filtered and the filter cake washed with n-heptane (36 mL, 3 vol.). The solids were allowed to dry overnight in a vacuum oven at 50-55° C. The 4-(6-amino-pyridin-3-yl)-piperazine-1-carboxylic acid tert-butyl ester was isolated as a pale orange solid (10.4 g collected; ~96% yield). $^1$H NMR (500 MHz, DMSO-$d_6$): δ 7.62 (dd, J=2.99, 0.60 Hz, 1H), 7.17 (dd, J=8.85, 2.99 Hz, 1H), 6.40 (dd, J=8.85, 0.60 Hz, 1H), 5.45 (bs, 2H), 3.43 (m, 2H), 2.85 (m, 2H), 1.41 (s, 9H); $^{13}$C NMR (125 MHz, DMSO-$d_6$): δ 154.8, 153.8, 138.7, 136.8, 125.9, 108.3, 78.9, 50.5, 43.8, 43.0, 28.0; HRMS: Calcd for $C_{14}H_{23}N_4O_2$ (M+H)$^+$: 279.18155, Found: 279.18173.

Example 2. Preparation of 6-bromo-2-chloro-8-cyclopentyl-5-methyl-8H-pyrido[2,3-d]pyrimidin-7-one

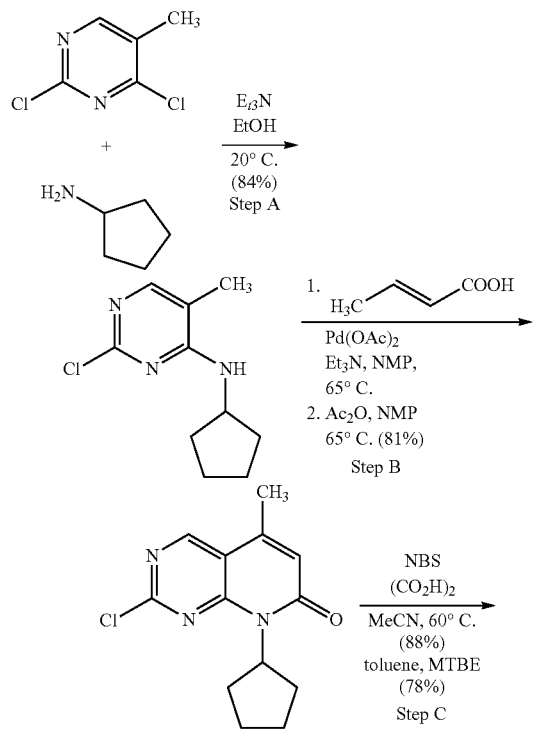

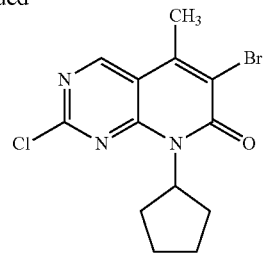

Step A. Preparation of 5-bromo-2-chloro-6-cyclopentylamino-pyrimidine

To a vessel was added absolute ethanol (3000 mL, 3.0 vol) followed by 5-bromo-2,4-dichloropyrimidine (mw 227.87; 1000 g, 1.0 equiv.). Triethylamine (612 mL, 1.0 equiv.) was added, and then cyclopentylamine (mw 85.15; 520 mL, 1.2 equiv.) was added slowly over 2 hours to control the mild exotherm. After completion of cyclopentylamine addition, the reaction was seeded with 5-bromo-2-chloro-6-cyclopentylamino-pyrimidine (5 g, 0.5 wt %) to induce crystallization, if needed. The reaction was stirred at 25° C. for 2 hours.

Water (2500 mL, 2.5 vol) was added to the vessel at 20-25° C. at a rate of 30 mL/min. The mixture was cooled to 8-12° C. at 2° C./min. The slurry was kept at 8-12° C. for 1 hour and then filtered onto a #2 Whatman™ paper filter. The cake was rinsed with n-heptane (2000 mL). The cake was reslurried with n-heptane on the filter drier (2000 mL). The material was dried overnight in the vacuum oven at 50-55° C. to give 5-bromo-2-chloro-6-cyclopentylamino-pyrimidine (1020 g; 84%) as a white solid.

Step B. Preparation of 2-chloro-8-cyclopentyl-5-methyl-8H-pyrido[2,3-d]pyrimidin-7-one To a vessel was added 5-bromo-2-chloro-6-cyclopentylamino-pyridimidine (10.0 g, 1.0 equiv.) along with N-methylpyrrolidone (NMP) (50 mL, 5.0 vol.) at ambient temperature. To the reaction mixture was added crotonic acid (4.7 g, 1.5 equiv.) and triethylamine (20.2 mL, 4.0 equiv.). The vessel was degassed and purged three times with nitrogen. To the degassed reaction mixture was added Pd(OAc)$_2$ (0.25 g, 0.03 equiv.). The vessel was degassed and purged three times with nitrogen using the same method as step 3. The mixture was heated to 65° C. and allowed to stir until starting material was consumed (at least 6 hours).

Acetic anhydride (6.8 mL, 2.0 equiv) was added to the reaction mixture. The reaction was allowed to react at 65° C. until starting material was consumed (usually 1-2 hours).

The reaction mixture was cooled to 20° C. and H$_2$O (100 mL, 10 vol) was added to dissolve triethylamine.HBr salts and precipitate out 2-chloro-8-cyclopentyl-5-methyl-8H-pyrido[2,3-d]pyrimidin-7-one. The material was granulated at 20° C. for 1 hour. The solids were filtered and washed with H$_2$O (20 mL, 2.0 vol), and a 4:1 mixture of isopropanol/H$_2$O (50 mL, 5.0 vol). The crude product was dried under vacuum at 55-70° C. to give 2-chloro-8-cyclopentyl-5-methyl-8H-pyrido[2,3-d]pyrimidin-7-one, (7.8 g; 81%) as a tan to gray solid.

Step C. Preparation of 6-bromo-2-chloro-8-cyclopentyl-5-methyl-8H-pyrido[2,3-d]pyrimidin-7-one To a glass lined vessel was added 2-chloro-8-cyclopentyl-5-methyl-8H-pyrido[2,3-d]pyrimidin-7-one (9.35 g, 1.0 equiv.) along with acetonitrile (65 mL, 7.0 vol). N-Bromosuccinimide (9.67 g, 1.5 equiv.) and oxalic acid (0.65 g, 0.2 equiv.) were added. The reaction mixture was heated to 60±5° C. The reaction was stirred at 60° C. until starting material was consumed (at least 6 hours). The slurry was cooled to 20° C. and $H_2O$ (9 mL, 1 vol) was added. To the slurry was added a solution of sodium bisulfite (3.88 g, 1.0 equiv) in $H_2O$ (38 mL, 4 vol). The slurry was granulated for 1 hour, then filtered directly onto a #2 Whatman paper filter. The reaction vessel was washed with water (19 mL, 2 vol) followed by a 7:3 mix of methanol/acetonitrile (28 mL, 3 vol), and the washes were transferred onto the filter cake. The product was dried in the vacuum oven at 50-55° C. 6-Bromo-2-chloro-8-cyclopentyl-5-methyl-8H-pyrido[2,3-d]pyrimidin-7-one (10.52 g; 87%) was isolated as a pale yellow solid.

The product was further purified by recrystallization from toluene and n-heptanes. Toluene (60 mL, 6 vol) and 6-bromo-2-chloro-8-cyclopentyl-5-methyl-8H-pyrido[2,3-d]pyrimidin-7-one (10.00 g, 1 equiv) were added to a reaction vessel and heated to 80° C. The warm reaction mixture was filtered through an appropriate cartridge to ensure the removal of insoluble Pd and other insoluble contaminants. The filter cartridge was washed with 80° C. toluene (5 mL, 0.5 vol). The slurry was cooled to 25° C. at 1° C./min. n-Heptane (70 mL, 7 vol) was added to the reaction slurry at 1 mL/min. The slurry was further cooled to 0° C. at 1° C./min. The slurry was granulated at 0° C. for at least 1 hour.

The slurry was filtered directly onto a #2 Whatman paper filter. n-Heptane (30 mL, 3 vol) was charged to the reaction vessel and the wash was transferred onto the filter cake and the product was dried in the vacuum oven at 50-55° C. 6-Bromo-2-chloro-8-cyclopentyl-5-methyl-8H-pyrido[2,3-d]pyrimidin-7-one (8.73 g, 87%) was isolated as a cream colored solid. $^1$H NMR (500 MHz, DMSO-$d_6$): δ 9.20 (s, 1H), 5.82 (m, 1H), 2.65 (s, 3H), 2.11 (m, 2H), 2.04 (m, 2H), 1.86 (m, 2H), 1.64 (m, 2H); $^{13}$C NMR (125 MHz, DMSO-$d_6$): δ 158.2, 158.2, 157.6, 154.1, 144.0, 120.9, 113.0, 54.4, 28.3, 25.7, 18.3; HRMS: Calcd for $C_{13}H_{14}N_3O_1Br_1Cl_1$ (M+H)$^+$: 342.00033, Found: 342.00037.

Example 3. Preparation of 4-{6-[6-bromo-8-cyclopentyl-5-methyl-7-oxo-7,8-dihydro-pyrido[2,3-d]pyrimidin-2-ylamino]pyridin-3-yl}-piperazine-1-carboxylic acid tert-butyl ester

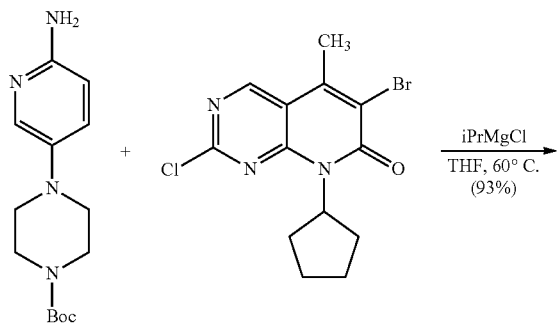

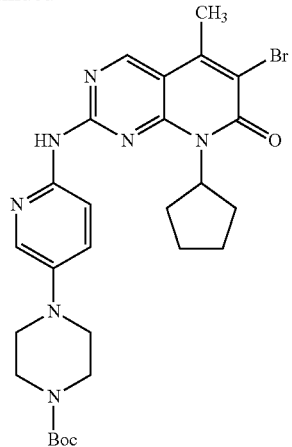

A dry, nitrogen purged reactor was charged with tetrahydrofuran (900 mL, 15 mL/g). The batch temperature was set at 20° C. and agitation at 250 RPM was started. The reactor was charged with 4-(6-amino-pyridin-3-yl)-piperazine-1-carboxylic acid tert-butyl ester (63.4 g, 0.2278 moles, 1.3 equiv.) and the mixture held at 20° C. for 30 min to dissolve the starting material. The reactor was charged with isopropylmagnesium chloride (93.9 g, 0.193 moles, 1st charge 1.1 eq) (2.0M in THF, 1.1 equiv.) by pump over 30 min. The batch was maintained at 20° C. for 40 min. The reactor was charged with 6-bromo-2-chloro-8-cyclopentyl-5-methyl-8H-pyrido[2,3-d]pyrimidin-7-one (60.1 g, 0.1755 moles, 1 eq.) all at once and rinsed with THF (50 mL rinse). An additional charge of isopropylmagnesium chloride (93.9 g, 0.193 moles, 1.1 eq—2nd charge (2.0M in THF, 1.1 equiv.) was added by pump over 30 min. The batch was held at 20° C. for 90 min. and then heated from 20° C. to 60° C.

After reaction, a mixture of THF (2.86 vol) and HOAc (1 equiv.) was used to quench the reaction. The batch was then seeded with 0.5 wt/wt % of 4-{6-[6-bromo-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester and a mixture of THF (1.14 vol) and HOAc (0.4 equiv.) was charged to complete the precipitation. After cooling to 20° C., the batch was filtered, washed with acetone (4 vol), water (6 vol) and acetone (4 vol).

The wet cake was dried under vacuum at 65° C. to a constant weight to give 4-{6-[6-bromo-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester in 93% yield. $^1$H NMR (600 MHz, THF-$d_8$): δ 9.36 (s, 1H), 8.87 (s, 1H), 8.22 (d, J=8.8 Hz, 1H), 8.04 (d, J=2.9 Hz, 1H), 7.39 (dd, J=8.8, 2.9 Hz, 1H), 6.10 (m, 1H), 3.55 (broad, 4H), 3.09 (broad, 4H), 2.60 (s, 3H), 2.30 (m, 2H), 2.09 (m, 2H), 1.85 (m, 2H), 1.66 (m, 2H), 1.46 (s, 9H); $^{13}$C NMR (150 MHz, THF-$d_8$): δ 159.5, 158.9, 157.7, 156.0, 155.0, 147.2, 144.62, 144.56, 138.0, 126.7, 117.6, 114.2, 108.4, 79.9, 55.5, 50.6, 44.7, 29.0, 28.7, 26.9, 18.1; HRMS: Calcd for $C_{27}H_{35}N_7O_3Br_1$ (M+H)$^+$: 584.19797, Found: 584.19811.

Example 4. Preparation of 4-{6-[6-(1-butoxyl-vinyl)-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester

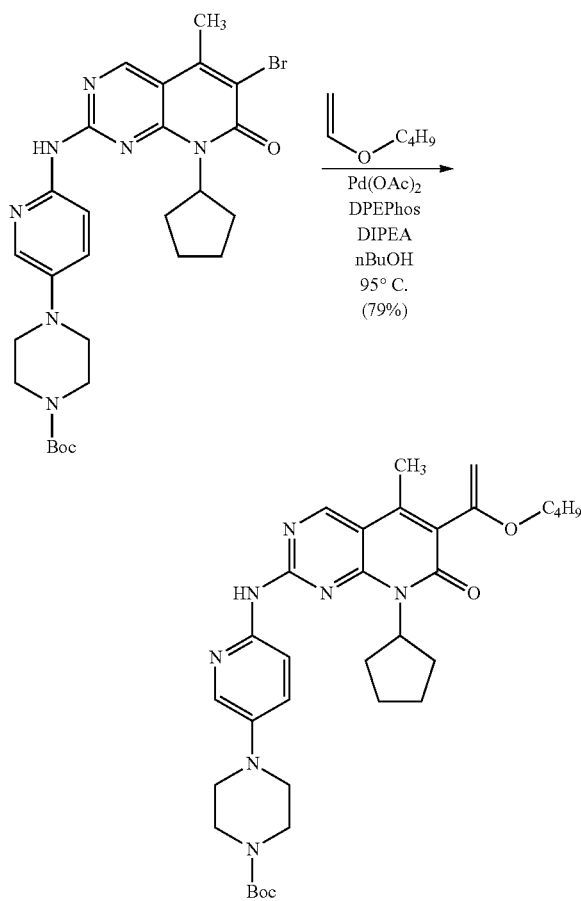

A dry, nitrogen-purged reactor was charged with 1-butanol (60 mL, 6 mL/g) and 4-{6-[6-bromo-8-cyclopentyl-5-methyl-7-oxo-7,8-dihydro-pyrido[2,3-d]pyrimidin-2-ylamino]-pyridin-3-yl}-piperazine-1-carboxylic acid tert-butyl ester (10 g, 0.017 moles) and butyl vinyl ether (5.1 g, 0.051 moles, 3.0 eq) were added. Diisopropylethylamine (5.3 g, 0.041 moles, 2.4 eq) was added and the mixture was sparged with nitrogen through a sparge tube for 30 minutes. Palladium acetate (0.16 g, 0.00068 moles, 0.0400 eq) and bis(2-diphenyphosphinophenyl)ether (0.45 g, 0.00082 moles, 0.04800 eq) were added. The mixture was heated to 95° C. over 30 minutes and the batch was stirred at 95° C. for 2 hours. The mixture was cooled to 80° C. and sampled to monitor reaction completion. Following completion, water (15 mL, 1.5 mL/g) and 1-butanol (30 mL, 3 mL/g) were added.

The solution was filtered through a 0.45 micron filter to remove precipitated palladium. Water (35 mL, 3.5 mL/g) was added, followed by 1,2 diaminopropane (6.3 g, 0.085 moles, 5.0 eq). The mixture was stirred at 70° C. for at least 30 minutes. The agitation was stopped and the mixture was allowed to settle for 15 minutes. The bottom aqueous phase was separated off and the mixture was cooled to 60° C. over 30 minutes. The mixture was seeded with 4-{6-[6-(1-butoxyl-vinyl)-8-cyclopentyl-5-methyl-7-oxo-7,8-dihydro-pyrido[2,3-d]pyrimidin-2-ylamino]pyridin-3-yl}-piperazine-1-carboxylic acid tert-butyl ester (Form C) (50 mg, 0.005 g/g) and held at 60° C. for 90 minutes.

Once crystallization was observed, the mixture was cooled to 50° C. over one hour and held at 50° C. for three hours. The mixture was cooled to 30° C. over three hours and held at 30° C. for two hours, then cooled to 20° C. over four hours and held at 20° C. for four hours. The slurry was filtered and washed with 1-butanol (10 mL, 1 mL/g). The filter cake was blown down and the mixture was charged with 1-butanol (10 mL, 1 mL/g) and the slurry was stirred at 20° C. for 1 hour. The filter cake was blown down. The mixture was washed with methyl t-butyl ether (20 mL, 2 mL/g) and the cake was fully deliquored using extended blow through times (2 hours or more). The cake was dried at 70° C. Yield is 75-80%. $^1$H NMR (600 MHz, DMSO-$d_6$): δ 10.0 (s, 1H), 8.87 (s, 1H), 8.07 (d, J=2.9 Hz, 1H), 7.91 (d, J=9.0 Hz, 1H), 7.48 (dd, J=9.0, 2.9 Hz, 1H), 5.83 (m, 1H), 4.47 (d, J=1.6 Hz, 1H), 4.05 (d, J=1.6 Hz, 1H), 3.77 (t, J=6.4 Hz, 2H), 3.48 (broad, 4H), 3.11 (broad, 4H), 2.37 (s, 3H), 2.22 (m, 2H), 1.89 (m, 2H), 1.75 (m, 2H), 1.61 (m, 2H), 1.58 (m, 2H), 1.43 (s, 9H), 1.38 (m, 2H), 0.90 (t, J=7.39 Hz, 3H); $^{13}$C NMR (150 MHz, DMSO-$d_6$): δ 160.9, 158.2, 157.3, 155.2, 154.6, 153.7, 145.0, 143.0, 142.6, 136.0, 125.8, 125.5, 114.6, 106.6, 87.8, 78.9, 66.8, 52.8, 48.5, 43.4, 42.5, 30.3, 28.0, 27.4, 25.1, 18.8, 14.4, 13.6; HRMS: Calcd for $C_{33}H_{46}N_7O_4$ (M+H)$^+$: 604.36058, Found: 604.36049.

The intermediate butoxyl-vinyl ether may be isolated in one of several polymorphic forms. Form A was isolated as the kinetic product in the absence of seeding, while Form B was isolated in a few cases but is rarely observed. The most stable crystalline form of the butoxyl-vinyl ether, Form C, was obtained by seeding the reaction mixture with Form C crystals. Any of these polymorphic forms may be utilized in the preparation of Compound 1 free base, but polymorph Form C of the butoxyl-vinyl ether is preferred for ease of filterability.

PXRD data for polymorph Forms A, B and C of the intermediate butoxyl-vinyl ether are tabulated in Tables 7, 8 and 9, respectively.

TABLE 7

PXRD data for polymorph Form A of intermediate butoxyl-vinyl ether

| 2θ (°) ± 0.2 | Peak Intensity (%) |
|---|---|
| 4.3 | 100 |
| 4.8 | 85 |
| 6.2 | 39 |

TABLE 8

PXRD data for polymorph Form B of intermediate butoxyl-vinyl ether

| 2θ (°) ± 0.2 | Peak Intensity (%) |
|---|---|
| 5.5 | 100 |
| 7.5 | 3 |
| 9.7 | 3 |
| 11.1 | 4 |
| 14.8 | 3 |
| 16.7 | 4 |
| 17.5 | 5 |
| 20.1 | 4 |

TABLE 9

PXRD data for polymorph Form C of intermediate butoxyl-vinyl ether

| 2θ (°) ± 0.2 | Peak Intensity (%) |
|---|---|
| 5.4 | 100 |
| 9.7 | 11 |
| 10.8 | 58 |
| 12.7 | 10 |
| 13.3 | 24 |
| 13.5 | 27 |
| 16.1 | 12 |
| 16.6 | 8 |
| 17.0 | 14 |
| 17.5 | 22 |
| 18.1 | 8 |
| 18.8 | 8 |
| 19.6 | 16 |
| 20.6 | 16 |
| 21.7 | 17 |
| 22.9 | 8 |
| 23.8 | 8 |
| 24.4 | 8 |
| 25.0 | 8 |

Example 5. Preparation of Small Particle Size Free Base of Compound 1 by Salt Break Method

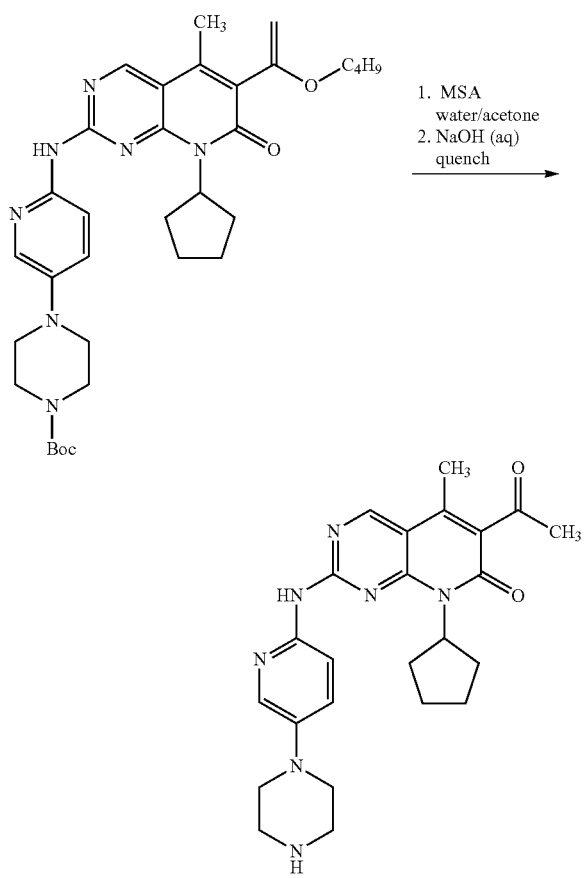

To a reactor was added 4-{6-[6-(1-butoxyl-vinyl)-8-cyclopentyl-5-methyl-7-oxo-7,8-dihydropyrido[2,3-d]pyrimidin-2-ylamino]-pyridin-3-yl}-piperazine-1-carboxylic acid tert-butyl ester (2.70 kg, 4.47 mol, 1.0 equiv.) followed by a mixture of water (27.00 L, 10 L/kg) and acetone (13.50 L, 5 L/kg). The yellow slurry was warmed to between 50° C. and 55° C. A solution of methanesulfonic acid (2.15 kg, 22.36 mol, 5.0 eq.) diluted with water (5.40 L, 2 L/kg of starting material) and acetone (5.40 L, 2 L/kg of starting material) was added to the reactor over approximately 10 minutes. The reaction mixture was kept between 45° C. and 55° C. for at least 12 hours. A clear yellow solution was achieved during the reaction.

The reaction mixture was cooled to 35° C., and a mixture of 5 wt % sodium hydroxide solution was added in portions to the reactor to raise the reaction mixture to a pH>9. The reactor was cooled to between 20° C. and 25° C., granulated, and filtered. The cake was washed with water followed by acetone and dried under vacuum.

This method generated the small primary particle size free base of compound 1, which was equivalent to the material prepared from treatment of the compound 1 hydrochloride salt with aqueous NaOH in Example 4 of WO 2005/005426.

In addition to the representative procedure provided above (corresponding to Experiment S in Table 10), a range of acids and aqueous solvent systems were screened to determine the impact on the reaction and subsequent quench and isolation of free base of compound 1. Lab-scale screening experiments were run to identify reaction conditions for converting the intermediate vinyl ether to the free base compound 1. The results of these reaction screening experiments are summarized in Table 10, indicating the generality of the method.

TABLE 10

Summary of results from reaction screening experiments

| Experiment | Acid | Solvent system | Yield | Purity |
|---|---|---|---|---|
| A | Isethionic acid | water | 99 | 99.93 |
| B | Isethionic acid | 16% THF/water | >100 | 98.77 |
| C | Isethionic acid | 28% THF/water | 95 | 97.95 |
| D | HCl | water | >100 | 99.59 |
| E | $H_2SO_4$ | water | 98 | 98.6 |
| F | MSA | water | 98 | 99.42 |
| G | MSA | 16% THF/water | >100 | 97.86 |
| H | Isethionic acid | 15% NMP/water | 88 | 97.7 |
| I | Isethionic acid | 15% DMF/water | 90 | 98.94 |
| J | TFA (8 eq.) | water | 100 | 99.14 |
| K | Isethionic acid | 15% $CH_3CN$/water | >100 | 99.56 |
| L | Isethionic acid | 15% acetone/water | 92 | 99.54 |
| M | Isethionic acid | 15% DMAC/water | >100 | 98.91 |
| N | Isethionic acid | 15% sulfolane/water | 92 | 98.67 |
| O | MSA | 15% $CH_3CN$/water | 100 | 99.52 |
| P | MSA | 15% acetone/water | 97 | 99.54 |
| Q | $CF_3SO_3H$ (incomplete) | water | N/A | N/A |
| R | MSA | 33% $CH_3CN$/water | 99 | 99.7 |
| S | MSA | 33% acetone/water | 98 | 99.74 |
| T | MSA | 33% MeOH/water | 98 | 99.74 |
| U | MSA | 33% THF/water | 96 | 99.76 |

Example 6. Conversion of Small Particle Size Free Base to Large Particle Size Free Base of Compound 1

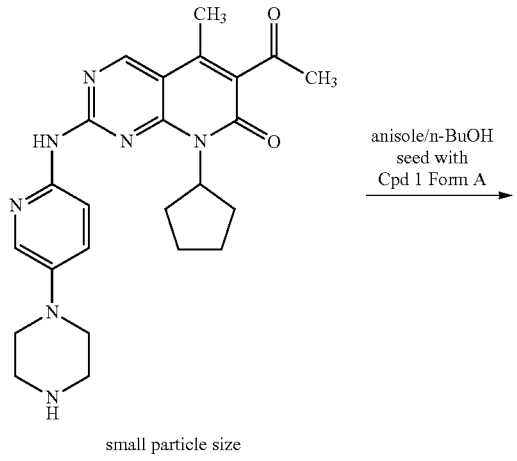

small particle size large particle size

To a reactor was added compound 1 free base (20 g, 44.69 mmol, 1.0 eq.), prepared according to Example 5, followed by 1-butanol (320 ml, 16 ml/g) and anisole (480 ml, 24 ml/g). The yellow slurry was warmed to between 95° C. and 10° C. to achieve dissolution. The reactor was cooled to 80° C. To the solution in the reactor, a seed slurry containing compound 1 free base (Form A) seed crystals (0.1 g, 0.2 mmol, 0.005 eq.) suspended in 1-butanol (5 mL, 0.25 mL/g of starting material) was charged to induce crystallization. The resulting slurry was stirred at 80° C. for 3 hours. The slurry was cooled to 10° C. at 0.2° C./min over 350 minutes, granulated, and filtered. The cake was washed with anisole followed by heptane, and dried under vacuum.

This method generated the large primary particle size crystals of the free base of compound 1, which were equivalent to the free base prepared using the one-pot method described in Example 7 below.

Example 7. One-Pot Method for Preparation of the Large Particle Size Free Base of Compound 1

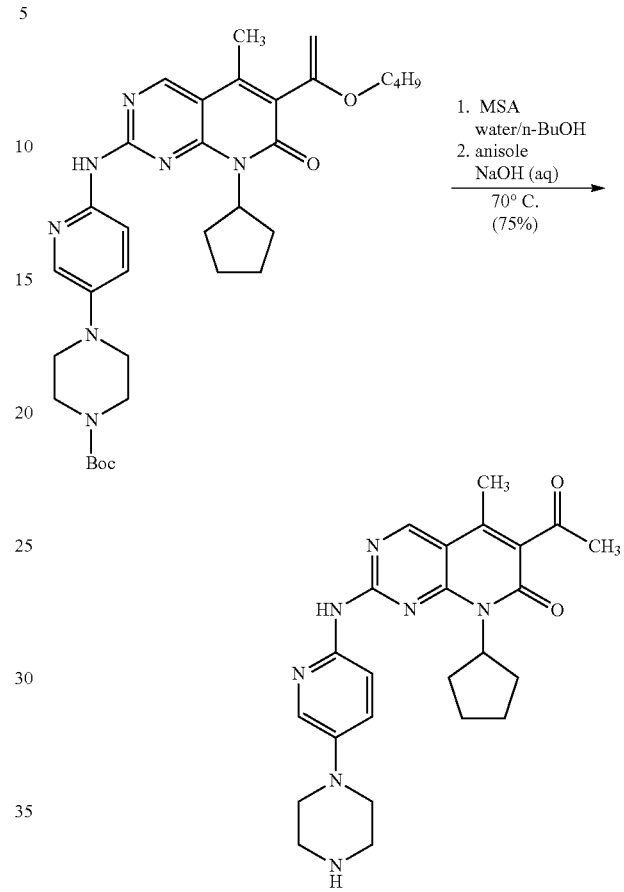

To a reactor was added water (200 mL, 10 mL/g) and 4-{6-[6-(1-butoxyl-vinyl)-8-cyclopentyl-5-methyl-7-oxo-7,8-dihydropyrido[2,3-d]pyrimidin-2-ylamino]-pyridin-3-yl}-piperazine-1-carboxylic acid tert-butyl ester (20 g, 33.1 mmol, 1.0 equiv.) followed by 1-BuOH (232 mL, 11.6 mL/g) to rinse any solids down into reactor. The yellow slurry was warmed to 70° C. A two-liquid phase mixture formed. Concentrated HCl solution (16.3 g, 165.5 mmol, 5.0 eq.) was added to the reactor over approximately 10 minutes. The reaction mixture was kept at 70° C. for 4 to 6 hours. A clear yellow biphasic solution was achieved after 3 hours.

To the reaction mixture was added anisole (356 mL, 17.8 mL/g). While maintaining the mixture at 70° C., a solution of aq. NaOH (17.2 g, 172.1 mmol, 5.2 eq.) (40 wt % solution) was added to the reactor over 20 minutes to raise the reaction mixture to a pH>10. The two-phase mixture was stirred for 30 minutes after the NaOH addition was complete.

The phases were separated and the organic phase was washed with water twice. The batch was then heated to 80° C. and speck-free filtered into the crystallizing vessel, rinsing the filter with butanol. The batch was then distilled to remove water and achieve a temperature of 120° C. The batch was then cooled to 80° C. and seeded with a seed slurry of compound 1 free base (Form A) seed crystals (0.015 g, 0.033 mmol, 0.1 wt. % wrt compound 1) and 1-BuOH (10 mL, 0.5 mL/g). The batch was then cooled to 30° C. at 0.2° C./min and then ripened with three cycles where the temperature was stepped down by 10° C. each time. On the final cycle, the batch was cooled to 10° C., granulated and filtered. The cake was washed with twice with heptane and dried under vacuum. After drying, the sample was confirmed to be a single crystalline polymorph Form A.

$^1$H NMR (600 MHz, DMSO-d$_6$/TFA): δ 10.41 (s, 0.75H), 9.03 (s, 0.25H), 8.98 (s, 2H), 8.12 (d, J=3.0 Hz, 1H), 7.90 (d, J=9.1 Hz, 1H), 7.63 (dd, J=9.1, 3.0 Hz, 1H), 5.84 (m, 1H), 3.40 (broad, 4H), 3.29 (broad, 4H), 2.43 (s, 3H), 2.33 (s, 3H), 2.21 (m, 2H), 1.91 (m, 2H), 1.79 (m, 2H), 1.59 (m, 2H); $^{13}$C NMR (150 MHz, DMSO-d$_6$/TFA): δ 202.4, 160.7, 154.8, 158.3, 158.0, 144.9, 142.3, 142.0, 134.6, 129.7, 126.7, 115.3, 107.0, 53.0, 45.6, 42.6, 31.3, 27.6, 25.2, 13.7; HRMS: Calcd for $C_{24}H_{30}N_7O_2$ (M+H)$^+$: 448.24555, Found: 448.24540.

Comparative PSA, SSA and surface energy data for the small primary particle size and large primary particle size formulations of the free base of compound 1 are provided below. In all cases, the free base was isolated as polymorph Form A.

Powder X-Ray Diffraction (PXRD)
Experimental:

Powder Diffraction analysis was conducted using a Bruker D8 diffractometer equipped with a Cu radiation source, fixed slits (divergence=1.0 mm, anti-scatter=0.6 mm, and receiving=0.6 mm) and a scintillation counter detector. Data were collected in the Theta-Theta goniometer at the Cu wavelength Kα$_1$=1.54056 Å from 3.0 to 40.0 degrees 2-Theta using a step size of 0.040 degrees and a step time of 2.0 second. X-ray tube voltage and amperage were set at 40 kV and 40 mA respectively. Samples were prepared by placement in a Nickel Disk (Gasser & Sons, Inc. Commack, N.Y.) and rotated during data collection. Data were collected and analyzed using Bruker DIFFRAC Plus software (Version 2.6). PXRD data files (.raw) were not processed prior to peak searching. Generally, a Threshold value of 1 and a Width value of 0.3 were used to make preliminary peak assignments. The output of automated assignments was visually checked to ensure validity and adjustments manually made if necessary. Additionally, peaks were manually assigned within spectra if appropriate.

SSNMR Experimental:

Carbon spectra on Form A were acquired on a 4 mm rotor for 2048 scans with recycle delay of 25 seconds and 2 ms of cross polarization. 100 kHz of proton decoupling was applied during acquisition. Carbon spectra on Form B were acquired on a 4 mm rotor for 2048 scans for 128 scans were collected with recycle delay of 4.5 seconds with 2 ms of cross polarization. 70 kHz of proton decoupling and total suppress of spinning sideband (TOSS) was applied during acquisition.

Instrument Method:

Approximately 80 mg of sample were packed into a 4 mm $ZrO_2$ rotor. Spectra were collected at ambient temperature and pressure on a Bruker-Biospin 4 mm CPMAS probe positioned into a wide-bore Bruker-Biospin Avance III 500 MHz ($^1$H frequency) NMR spectrometer. The packed rotor was oriented at the magic angle and spun at 15.0 kHz. The $^{13}$C solid state spectra were collected using a proton phase modulated decoupled cross-polarization magic angle spinning (CPMAS) experiment. The cross-polarization contact time was set to 2.0 ms. A proton decoupling field of approximately 100 kHz was applied during acquisition. The carbon spectrum of compound 1 Form A was acquired for 512 scans with a 25 second recycle delay. The spectrum is shown FIG. 2 and the data is tabulated in Table 2. The carbon spectrum of compound 1 Form B was acquired for 2048 scans with a 4.5 second recycle delay. The carbon spectra were referenced using an external standard of crystalline adamantane, setting its upfield resonance to 29.5 ppm. The spectrum is shown FIG. 4 and the data is tabulated in Table 4.

Particle Size Analysis

The particle size was analyzed using the laser diffraction (or small angle light scattering) technique by dispersing the dry sample powder with compressed air. Specifically, the particle size distribution was analyzed using the Sympatec HELOS RODOS system equipped with a Vibri dry powder feeder. The powder sample was dispersed with a dispersion pressure of 0.5 bar. In some instances, an Aspiros micro-dosing device was used, and the powder sample was dispersed with a dispersion pressure of 0.2 bar. A suitable lens was selected to cover the particle size range of each sample.

Results

Comparative data for four batches of API are provided in Table 11 below, using either the Vibri or Aspiros devices to disperse the sample. Batch No. 4 had a D90 of around 75 µm, whereas Batch Nos. 1 and 2 both had a D90 of approximately 45 µm. The laser diffraction particle size data confirms the SEM observations for these batches.

TABLE 11

Comparative Size Distribution Data

Summary of PSD data

| Batch No. | Disp. Method. | Particle size (µm) | | | |
|---|---|---|---|---|---|
| | | D [v, 0.1] | D [v, 0.5] | D [v, 0.9] | D [4, 3] |
| 1 | 0.2 Bar ASPIROS | 5.21 | 17.00 | 43.59 | 21.33 |
| 2 | 0.2 Bar ASPIROS | 6.20 | 20.83 | 46.15 | 23.87 |
| 3 | 0.2 Bar ASPIROS | 11.64 | 46.08 | 130.26 | 59.07 |
| | 0.5 bar VIBRI | 9.96 | 41.23 | 116.43 | 53.02 |
| 4 | 0.2 Bar ASPIROS | 7.41 | 24.97 | 76.56 | 35.06 |
| | 0.5 Bar VIBRI | 6.33 | 23.19 | 69.20 | 32.16 |

Scanning Electron Microscopy (SEM)

Figure 5:
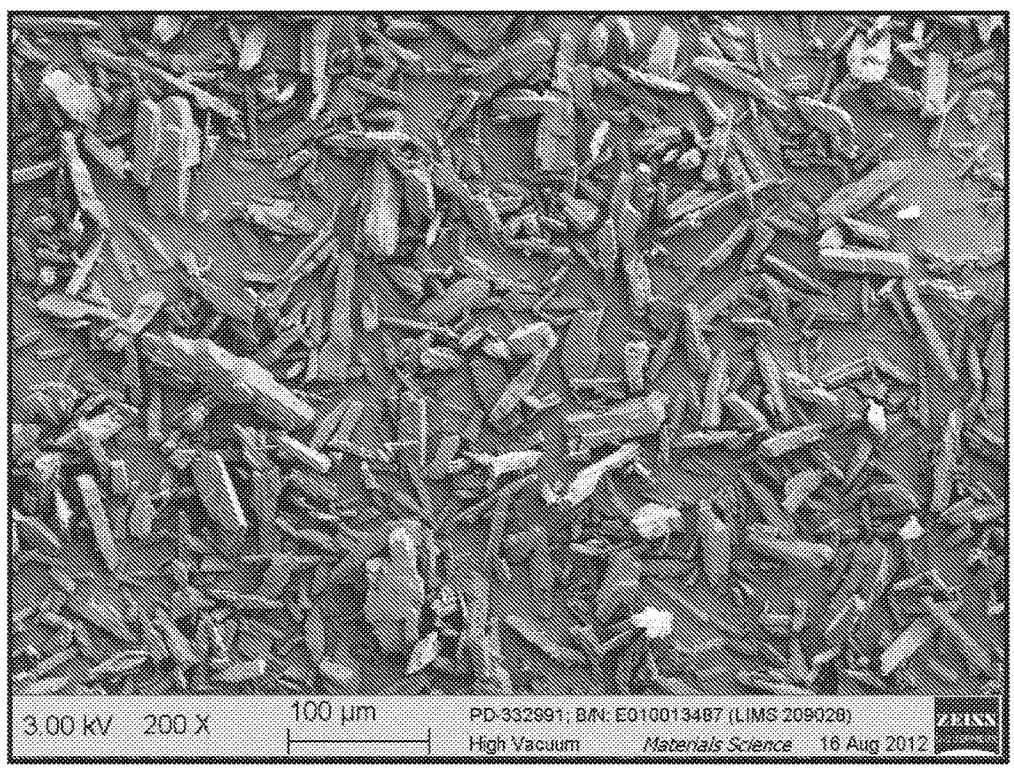
FIG. 5 shows a scanning electron microscopy (200× magnification) image of compound 1 free base API, polymorph Form A, recrystallized from 40% n-BuOH/anisole.

Scanning Electron Microscopy was performed under standard conditions. FIG. 5 provides a SEM (200× magnification) image of compound 1 free base Form A recrystallized from 40% BuOH/anisole. FIG. 6 provides a SEM (1500× magnification) image of compound 1 free base Form A isolated from a standard free basing process Sticking Analysis The MASS (Material Adhesion Screen for Sticking) Punch was developed in-house to quantitatively assess the sticking propensity of tablet formulations by weighing the amount of adhered powder on removable punch tip after a series of compressions. This test enables formulators to objectively and quickly evaluate the risk of punch sticking during drug product development and troubleshoot sticking observed during clinical tablet manufacturing.

To prepare the sample for MASS Punch testing, 10 g of API was diluted in a lightly lubricated standard blend (10% API, 89.75% Avicel PH102 and 0.25% magnesium stearate) and bottle blended (500 mL amber glass bottle) for 500 rotations. The weight of powder adhered to the removable punch tip (½" round flat faced) was assessed using a microbalance periodically up to 100 compressions of ~250 mgW tablets at a target solid fraction of 0.85.

The MASS Punch profile for compound 1 free base mixed in the standard blend showed a positive response. Photos of the punch tips at the end of the compression runs confirmed that powder adhered to the tips (data not shown). For reference, a control sample of the standard blend is not sticky and would have less than 10 μg powdered adhered. The test method was found to rank the sticking propensity of new API lots relative to those of known materials.

Specific Surface Area (SSA) Measurement (BET Nitrogen)
Apparatus

Specific Surface Area (SSA) measurement (BET Nitrogen) were determined using a Micromeritics TriStar II 3020 specific surface area analyser together with Micromeritics SmartPrep station (Micromeritics U.K. Ltd., Ste 2, The Stables Hexton Manor, Hexton, Hertfordshire SG5 3JH, England). Samples were subjected to the BET-nitrogen adsorption analysis to determine the specific surface area of the samples.

Setup

Software version: TriStar II Confirm (1.03 or equivalent)
Adsorbate: Nitrogen
Sample tube: ⅜" mm flat bottom cell with glass filler rods
Sample masses*: Approximately ¾ full cell
Sample preparation: SmartPrep (Flow degassing using nitrogen)
Out gassing conditions: 16 hrs at 25° C. under gas flow (ramping at 10° C./min)
Isothermal jacket: Used
Isothermal collection points: 11 point BET in the range 0.05-0.30 P/Po
Isothermal data analysis range: 7 point BET in the range 0.05-0.20 P/Po
Leak test: 120 s
Free space: Measured
Evacuation time: 1 hr
Outgas test duration: 180 s
Equilibration interval: 10 s
Equilibration timeout: 600 s The mass of sample varies according to the particle size of the test sample. For samples where the particle size is relatively small, approximately 0.50 g of material was required to fill the cell bulb, and where the particle size of the sample is relatively large, 0.75 g of material was required to ¾ fill the cell bulb.

Calculations and Reporting

The specific surface area was reported in the range 0.05-0.20 P/Po using 7 point BET from a triplicate determination. The sample mass, specific surface area, BET constant ('C' value) and correlation coefficient for each replicate were determined.

Results

Table 12 provides BET-N2 SSA for four batches of compound 1 free base API, one comprising the small primary particle size API prepared by the traditional salt break method (batch 5), and three batches comprising the large particle size API prepared according to the present invention. Batch 5 contained compound 1 free base having small primary particles and large agglomerates, which was very static-prone and sticky. Batch 6 was prepared using temperature cycling and had a typical particle size distribution (PSD) for the large particle size free base of compound 1, with a VMD of approximately 17 μm. Batch 7 demonstrated a similar PSD to batch 6. Batch 8 is a representative ICH batch of the large particle size free base of compound 1, also prepared by temperature cycling. The same batches were used in the surface energy determinations below.

TABLE 12

| BET SSA by $N_2$ | |
|---|---|
| Batch No. | BET SSA by $N_2$ |
| 5 | 6.6 |
| 6 | 0.62 |
| 7 | 0.69 |
| 8 | 0.67 |

Inverse-Phase Gas Chromatography (IGC) Surface Energy Measurement:

A sufficient quantity of sample was packed into a silanised glass column with the powder mass secured within the column by glass wool plugs inserted at both ends. The column was conditioned by flowing a stream of dry nitrogen through the powder mass for sufficient time for any surface adsorbates to be removed. Measurements were made by injecting a series of alkane vapour probes (Nonane, Octane, Heptane and Hexane) into the carrier gas stream at concentrations low enough to assume infinite dilution of the alkane vapour in the nitrogen stream and recording the time taken for each vapour to elute through the column. A plot of the retention time (corrected for the 'dead volume' of interstitial space within the packed column) versus a function of the cross sectional area and surface tension of the alkane vapour probe molecules used yields a line with a slope indicative of the surface energy of the solid powder under examination.

Results

Table 13 provides Dispersive Surface Energy (mJ/m²) data generated for the four batches of compound 1 free base, i.e., batches 5-8, described above with respect to the SSA data. Batch 5 is the small particle size free base, and batches 6-8 include the large particle size of the free base API.

TABLE 13

| Dispersive Surface Energy (mJ/m$^2$) | |
|---|---|
| Batch No. | Dispersive Surface Energy (mJ/m$^2$) |
| 5 | 61.63 |
| 6 | 49.42 |
| 7 | 35.75 |
| 8 | 42.27 |

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A crystalline free base of 6-acetyl-8-cyclopentyl-5-methyl-2-(5-piperazin-1-yl-pyridin-2-ylamino)-8H-pyrido[2,3-d]pyrimidin-7-one, having a powder X-ray diffraction pattern comprising peaks at diffraction angles (2θ) of 8.0±0.2, 10.1±0.2 and 11.5±0.2 and a primary particle size distribution characterized by a D90 value of from about 30 μm to about 65 μm.

2. The free base of claim 1, having a powder X-ray diffraction pattern comprising peaks at diffraction angles (2θ) of 8.0±0.2, 10.1±0.2, 10.3±0.2, and 11.5±0.2.

3. The free base of claim 1, having a powder X-ray diffraction pattern comprising peaks at diffraction angles (2θ) essentially the same as shown in FIG. 1.

4. The free base of claim 1, having a $^{13}$C solid state NMR spectrum comprising the following resonance (ppm) values: 12.5 ppm±0.2 ppm.

5. The free base of claim 4, having a $^{13}$C solid state NMR spectrum comprising the following resonance (ppm) values: 12.5 ppm and 112.4 ppm±0.2 ppm.

6. The free base of claim 5, having a $^{13}$C solid state NMR spectrum comprising the following resonance (ppm) values: 12.5 ppm, 112.4 ppm and 143.2 ppm±0.2 ppm.

7. A crystalline free base of 6-acetyl-8-cyclopentyl-5-methyl-2-(5-piperazin-1-yl-pyridin-2-ylamino)-8H-pyrido[2,3-d]pyrimidin-7-one, having a powder X-ray diffraction pattern comprising peaks at diffraction angles (2θ) of 8.0±0.2, 10.1±0.2 and 11.5±0.2 and a volume mean diameter characterized by a D[4,3] value of from about 15 μm to about 40 μm.

8. The free base of claim 7, having a powder X-ray diffraction pattern comprising peaks at diffraction angles (2θ) of 8.0±0.2, 10.1±0.2, 10.3±0.2, and 11.5±0.2.

9. The free base of claim 7, having a powder X-ray diffraction pattern comprising peaks at diffraction angles (2θ) essentially the same as shown in FIG. 1.

10. The free base of claim 7, having a $^{13}$C solid state NMR spectrum comprising the following resonance (ppm) values: 12.5 ppm±0.2 ppm.

11. The free base of claim 10, having a $^{13}$C solid state NMR spectrum comprising the following resonance (ppm) values: 12.5 ppm and 112.4 ppm±0.2 ppm.

12. The free base of claim 11, having a $^{13}$C solid state NMR spectrum comprising the following resonance (ppm) values: 12.5 ppm, 112.4 ppm and 143.2 ppm±0.2 ppm.

13. A pharmaceutical composition comprising the free base of claim 1 and at least one pharmaceutically acceptable carrier, diluent or excipient.

14. A pharmaceutical composition comprising the free base of claim 7 and at least one pharmaceutically acceptable carrier, diluent or excipient.

15. A crystalline free base of 6-acetyl-8-cyclopentyl-5-methyl-2-(5-piperazin-1-yl-pyridin-2-ylamino)-8H-pyrido[2,3-d]pyrimidin-7-one, having a powder X-ray diffraction pattern comprising peaks at diffraction angles (2θ) of 8.0±0.2, 10.1±0.2 and 11.5±0.2 and a volume mean diameter characterized by a D[4,3] value of from about 15 μm to about 30 μm.

16. The free base of claim 15, having a powder X-ray diffraction pattern comprising peaks at diffraction angles (2θ) of 8.0±0.2, 10.1±0.2, 10.3±0.2, and 11.5±0.2.

17. The free base of claim 15, having a powder X-ray diffraction pattern comprising peaks at diffraction angles (2θ) essentially the same as shown in FIG. 1.

18. The free base of claim 15, having a $^{13}$C solid state NMR spectrum comprising the following resonance (ppm) values: 12.5 ppm±0.2 ppm.

19. The free base of claim 18, having a $^{13}$C solid state NMR spectrum comprising the following resonance (ppm) values: 12.5 ppm and 112.4 ppm±0.2 ppm.

20. The free base of claim 19, having a $^{13}$C solid state NMR spectrum comprising the following resonance (ppm) values: 12.5 ppm, 112.4 ppm and 143.2 ppm±0.2 ppm.

21. A pharmaceutical composition comprising the free base of claim 15 and at least one pharmaceutically acceptable carrier, diluent or excipient.

* * * * *